(12) United States Patent
Nakanishi et al.

(10) Patent No.: US 6,576,623 B1
(45) Date of Patent: *Jun. 10, 2003

(54) SILICONE COMPOUND AND COSMETIC MATERIALS CONTAINING THE SAME

(75) Inventors: Tetsuo Nakanishi, Gunma-Ken (JP); Ichiro Ono, Gunma-Ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/628,946

(22) Filed: Jul. 31, 2000

(30) Foreign Application Priority Data

Jul. 30, 1999  (JP) .......................................... 11-216619

(51) Int. Cl.$^7$ ...................... A01N 55/00; A61K 31/695; A61K 31/74; A61K 6/00; A61K 7/00; C07F 7/04; C07F 7/08; C07F 7/18

(52) U.S. Cl. ...................... 514/63; 424/401; 424/78.03; 556/443

(58) Field of Search ............................ 524/588; 528/25, 528/31; 556/443; 424/401, 78.03; 514/63

(56) References Cited

U.S. PATENT DOCUMENTS

| | | | | |
|---|---|---|---|---|
| 4,558,112 A | * | 12/1985 | Talcott | 538/31 |
| 4,631,208 A | * | 12/1986 | Westall | 427/387 |
| 4,832,944 A | * | 5/1989 | Socci et al. | 424/61 |
| 5,210,133 A | * | 5/1993 | O'Lenick, Jr. | 525/54.1 |
| 5,288,831 A | * | 2/1994 | Ichinohe et al. | 528/25 |
| 5,310,842 A | * | 5/1994 | Ichinohe et al. | 528/12 |
| 5,470,900 A | * | 11/1995 | Sasaki et al. | 524/269 |
| 5,557,000 A | * | 9/1996 | Minemura | 556/434 |
| 5,565,194 A | * | 10/1996 | Burkhart et al. | 424/70.12 |
| 5,625,023 A | * | 4/1997 | Chung et al. | 528/29 |
| 5,625,024 A | * | 4/1997 | Schlitte et al. | 528/29 |
| 5,696,192 A | * | 12/1997 | Harashima | 524/366 |
| 5,712,335 A | * | 1/1998 | Tsuda et al. | 524/269 |
| 6,132,743 A | * | 10/2000 | Kuroda et al. | |
| 6,133,370 A | * | 10/2000 | Gutek et al. | 556/445 |

FOREIGN PATENT DOCUMENTS

| | | |
|---|---|---|
| EP | 0 298 402 | 1/1989 |
| EP | 0 501 791 | 9/1992 |
| EP | 0 545 002 | 6/1993 |
| EP | 0 665 227 A2 * | 1/1995 |
| EP | 1 062 944 | 12/2000 |
| EP | 1 065 234 | 1/2001 |

\* cited by examiner

*Primary Examiner*—Sreeni Padmanabhan
*Assistant Examiner*—Lauren Q. Wells
(74) *Attorney, Agent, or Firm*—Millen, White, Zelano & Branigan, P.C.

(57) ABSTRACT

A silicone compound useful in cosmetic materials and skin cleansing compositions which have no oily feel although they spread easily and smoothly, give moist, fresh and dry feelings to the users, have durable effects, and are highly stable to temperature changes and long-term storage. They additionally also absorb makeup cosmetics and sebum stains well when used in a skin-cleansing composition.

21 Claims, No Drawings

SILICONE COMPOUND AND COSMETIC MATERIALS CONTAINING THE SAME

BACKGROUND OF THE INVENTION

The present invention relates to a silicone compound having high affinity for various unctuous agents, such as silicone oils, and excellent emulsifying capability, and further to cosmetic materials containing such a silicone compound.

FIELD OF THE INVENTION

In recent years, silicone oils have been used as an unctuous agent mixed in emulsified compositions of water-in-oil type to ensure no greasiness, less tackiness and good water repellency for the emulsified compositions. However, it is still difficult to impart good stability to water-in-oil emulsions containing silicone oils by the use of conventional emulsifiers, such as polyoxyalkylene fatty acid esters.

So the methods of using polyoxyalkylene-modified organopolysiloxanes (polyether-modified silicones) highly compatible with silicone oils as surfactants in water-in-oil emulsions have been proposed in, e.g., JP-A-61-293903, JP-A-61-293904, JP-A-62-187406, JP-A-62-215510 and JP-A-62-216635 (the term "JP-A" as used herein means an "unexamined published Japanese patent application). However, not only silicone oils alone but also mixtures with ester oils and hydrocarbon oils are used in many of emulsions for cosmetics use. In water-in-oil emulsions using those oil mixtures as an unctuous agent, the foregoing polyether-modified silicone surfactants have inferior power of emulsification, so they are difficult to impart satisfactory stability to the emulsions of the aforementioned type.

As a method for solving the foregoing problem, the method of using as an emulsifier an organopolysiloxane having both long-chain alkyl and polyoxyalkylene groups, which is represented by the following formula, is proposed in JP-A-61-90732.

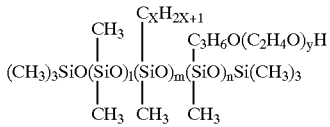

Although the organopolysiloxane compounds represented by the foregoing formula have excellent emulsifying power in systems containing mixed oils rich in ester oil and hydrocarbon oil, they have a drawback of sometimes failing to ensure high stability and no change upon storage for the systems containing mixed oils rich in silicone oils. Therefore, it has been desired to develop emulsifiers suitable for cosmetic materials, namely compounds having excellent capability to emulsify conventional unctuous agents, such as silicone oils, ester oils and hydrocarbon oils, for general cosmetics use to ensure high storage stability of the cosmetic materials.

SUMMARY OF THE INVENTION

A first object of the present invention is to provide a silicone compound having a great capability to emulsify various unctuous agents, including silicone oils, for cosmetics use and ensuring high emulsion stability.

A second object of the invention is to provide a cosmetic material which has high stability in an emulsified state to ensure satisfactory storage stability.

As a result of our intensive studies to attain the aforementioned objects, it has been found that the silicone compounds produced by addition of polyoxyalkylene compounds and silicone compounds to organohydrogenpolysiloxanes have a very strong affinity for silicone oils to ensure a great capability to emulsify them, and so when they are used as emulsifier the resultant emulsions can have very good stability. Further, it has also been found that the silicone compounds produced by addition of long-chain alkyl group-containing organic compounds besides polyoxyalkylene compounds and silicone compounds to organohydrogenpolysiloxanes have a very strong affinity for unctuous agents used in general cosmetic materials, including silicone oils, ester oils and hydrocarbon oils, to ensure a great capability to emulsify them, and so when they are used as emulsifier the resultant emulsions can have very good stability and a high degree of effectiveness for cosmetics use, thereby achieving the present invention.

While such silicone compounds as to be produced by the addition reaction of silicone compounds to organohydrogenpolysiloxanes are disclosed in JP-A-7-197055 as actuation silicone oils having good low temperature characteristics, it is our finding that those silicone compounds are particularly effective as ingredients of cosmetic materials. Further, we have found that, when the aforementioned silicone compounds have relatively low molecular weight, they are instrumental in cleansing not only sebum stains but also makeup stains from cosmetics of the type which are hard to come off, and besides, the cleansing composition comprising them has a very good touch during and after cleansing treatment.

The present invention thus provides a silicone compound represented by the following formula (1), and cosmetic materials containing such a silicone compound:

$$R^1_a R^2_b R^3_c SiO_{(4-a-b-c)/2} \qquad (1)$$

wherein

R$^1$ groups, which are the same or different, are each an organic group selected from the class consisting of 1–30C alkyl groups, aryl groups, aralkyl groups, fluorinated alkyl groups and organic groups represented by the following formula (2),

R$^2$ groups are polyoxyalkylene moiety-containing organic groups represented by the following formula (3),

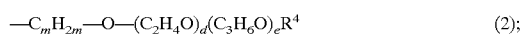

R$^3$ groups are organosiloxane compound residues represented by the following formula (4),

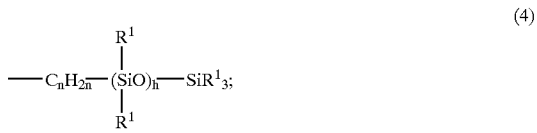

R$^4$ represents a 4–30C hydrocarbon group or an acyl group represented by R$^6$—CO—; R$^5$ represents a hydrogen atom, a 1–30C hydrocarbon group or an acyl group represented by R$^6$—CO—; R$^6$ represents a 1–30C hydrocarbon group; a, b and c are values in the ranges $1.0 \leq a \leq 2.5$, $0.001 \leq b \leq 1.5$ and $0.001 \leq c \leq 1.5$; d and e are each an integer of from 0 to 50; f is an integer of from 2 to 200 and g is an integer of from 0 to 200, provided that the sum of f and g is an integer of from 3 to 200; m is an integer of from 0 to 15; h is an integer of from 0 to 500; and n is an integer of from 1 to 5.

DETAILED DESCRIPTION OF THE INVENTION $R^1$ groups in formula (1) may be the same or different, and each of them represents a 1–30C alkyl group, an aryl group, an aralkyl group, a fluorinated alkyl group or an organic group represented by formula (2). Examples of an alkyl group represented by $R^1$ include methyl, ethyl, propyl, butyl, pentyl, hexyl, heptyl octyl, nonyl, decyl, cyclopentyl and cyclohexyl groups; those of an aryl group include phenyl and tolyl groups; those of an aralkyl group include benzyl and phenetyl groups; and those of a fluorinated alkyl group include trifluoropropyl and heptadecafluorodecyl groups.

The organic group $-C_mH_{2m}-O-(C_2H_4O)_d(C_3H_6O)_eR^4$ (formula (2)), represented by $R^1$ includes an alkoxy group, an acyloxy group, an alkenyl ether residue and an alkenyl ester residue. Additionally, $R^4$ in formula (2) represents a monovalent 4–30C hydrocarbon group or an acyl group of formula $R^6CO-$ (wherein $R^6$ is a 1–30C hydrocarbon group), d and e in formula (2) are each an integer of from 0 to 50, and m in formula (2) is an integer of from 0 to 15.

More specifically, when m, d and e are all zero, the formula (2) represents a 4–30 C alkoxy group including from lower alkoxy groups, such as butoxy and pentoxy, to higher alkoxy groups such as oleyloxy and stearoxy, or an acyloxy group such as a residue of acetic, lactic, butyric, oleic, stearic or behenic acid.

When m is not zero but d and e are zero, m is preferably 3, 5 or 11. In such a case, $R^1$ represents a 1- or 2-propenyl ether residue, a pentenyl ether residue, or an undecenyl ether residue. When $R^4$ is a hydrdocarbon group, such an ether residue is, e.g., an allyl stearyl ether residue, a pentenyl behenyl ether residue or an undecenyl oleyl ether residue. When d or e is not zero, the formula (2) assumes such a form that polyoxyalkylene is cut in an ether or ester linkage.

When m is 0, irrespective of the values of d and e, $R^1$ of formula (2) tends to have inferior resistance to hydrolysis; while, when m is greater than 15, the resultant silicone compound has a strong oily smell. It is therefore advantageous for m to be from 3 to 11.

For the present silicone compound, it is desirable that at least 50% of $R^1$ groups, preferably at least 70% of $R^1$ groups, be methyl groups. Also, 100% of $R^1$ groups in the present silicone compound may be methyl groups.

$R^2$ groups are polyoxyalkylene moiety-containing organic groups of formula $-C_mH_{2m}-O-(C_2H_4O)_f(C_3H_6O)_gR^5$ (formula (3)). $R^5$ in formula (3) is a hydrogen atom, a 1–30C hydrocarbon group or an acyl group represented by $R^6CO-$ wherein $R^6$ is a 1–30C hydrocarbon group. The letter f in formula (3) is an integer from 2 to 200, preferably from 5 to 100, and the letter g in formula (3) is an integer of from 0 to 200, preferably from 0 to 100, provided that the sum of f and g is in the range of 3 to 200, preferably 5 to 100. When $f/g \geq 1$, $R^2$ groups can impart high affinity for water enough to form a water-in-oil emulsion to the present silicone compound. When both ethylene oxide units and propylene oxide units constitute the polyoxyalkylene moiety in formula (3), those units may take the form of either block or random copolymer.

$R^3$ groups in formula (1) are organosiloxane compound residues represented by the following formula (4):

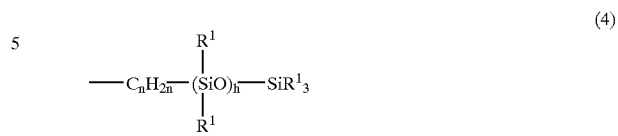

wherein $R^1$ has the same meaning as in formula (1), and h is an integer of from 0 to 500, preferably from 3 to 100, and n is an integer of from 1 to 5. For instance, n is 2 when the $R^3$ group is a residue of the organosiloxane compound prepared by reaction of vinyl group with a hydrogensiloxane compound. In the case where h is greater than 500, the organosiloxane compounds tend to have a problem that their reactivity to organohydrogenpolysiloxane to constitute the main chain of the present silicone compound become low.

In formula (1), the letter a represents a value of from 1.0 to 2.5, preferably from 1.2 to 2.3. When the letter a is smaller than 1.0, the silicone compound is inferior in compatibility with an unctuous agent, and so it is difficult to ensure satisfactory stability in water-in-oil emulsions. When the letter a is greater than 2.5, on the other hand, the silicone compound has poor affinity for water, so it is also difficult to ensure satisfactory stability in water-in-oil emulsions. The letter b in formula (1) represents a value of from 0.001 to 1.5, preferably from 0.05 to 1.0. When b is smaller than 0.001, the silicone compound has poor affinity for water, and so it is difficult to ensure satisfactory stability in water-in-oil emulsions; while, when b is greater than 1.5, the silicone compound has too high affinity for water to impart satisfactory stability to water-in-oil emulsions. The letter c in formula (1) represents a value of from 0.001 to 1.5, preferably from 0.05 to 1.0. When c is smaller than 0.001, the silicone compound is inferior in compatibility with silicone oils, and so it is difficult to ensure satisfactory stability in water-in-oil emulsions. When c is greater than 1.5, on the other hand, the silicone compound has poor affinity for water, so it is also difficult to ensure satisfactory stability in water-in-oil emulsions.

When the present silicone compound is employed as an emulsifier, it has no particular restriction as to weight average molecular weight, but its weight average molecular weight is preferably in the range of 500 to 200,000, particularly 1,000 to 100,000.

In the cases where the present silicone compound is mixed in skin cleansing compositions, on the other hand, its appropriate weight average molecular weight is at most 4,000, preferably at most 2,000, particularly preferably at most 1,500.

The present silicone compound represented by formula (1) can be easily synthesized by subjecting organohydrogenpolysiloxanes to addition reaction with a polyoxyalkylene compound represented by the following formula (5) and an organosiloxane compound represented by the following formula (6), and further, if desired, an alkylene compound and/or an organic compound represented by the following formula (7) in the presence of a platinum or rhodium catalyst:

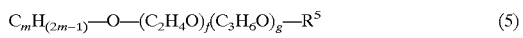
$$C_mH_{(2m-1)}-O-(C_2H_4O)_f(C_3H_6O)_g-R^5 \quad (5)$$

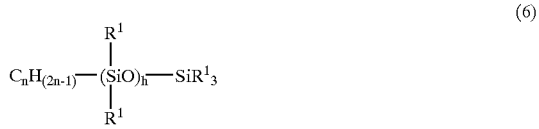
$$C_nH_{(2n-1)}-(SiO)_h^{\overset{R^1}{\underset{R^1}{|}}}-SiR^1_3 \quad (6)$$

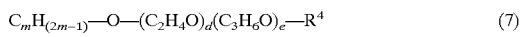
$$C_mH_{(2m-1)}-O-(C_2H_4O)_d(C_3H_6O)_e-R^4 \quad (7)$$

wherein $R^1$, $R^4$, $R^5$, d, e, f, g, h, m and n have the same meanings as defined above respectively.

The organohydrogenpolysiloxanes used in the foregoing addition reaction may be either straight-chain or cyclic ones. From the viewpoint of smooth progress of the addition reaction, straight-chain organohydrogenpolysiloxanes are used to advantage.

In the addition reaction, it is appropriate to use the foregoing compounds in such amounts that the ratio of the total amount of compounds to be added, namely polyoxyalkylene compounds of formula (5), organosiloxane compounds of formula (6), and alkylene compounds and/or organic compounds of formula (7), to the amount of organohydrogenpolysiloxanes is from 0.5 to 2.0, preferably from 0.8 to 1.2, expressed in terms of the total mole number of terminal unsaturated bonds present in the compounds per mole of SiH groups.

The addition reaction is effectively performed in the presence of a platinum catalyst or a rhodium catalyst. Suitable examples of such a catalyst include chloroplatinic acid, alcohol-modified chloroplatinic acid, and chloroplatinic acid-vinylsiloxane complex. The amount of catalyst used, though may be a catalytic amount, is specifically at most 50 ppm, preferably at most 20 ppm, based on the platinum or rhodium.

The aforementioned addition reaction may be carried out in an organic solvent, if desired. Examples of an organic solvent usable therein include aliphatic alcohols, such as methanol, ethanol, 2-propanol and butanol; aromatic hydrocarbons, such as toluene and xylene; aliphatic or alicyclic hydrocarbons, such as n-pentane, n-hexane and cyclohexane; and halogenated hydrocarbons, such as dichloromethane, chloroform and carbon tetrachloride. In the case of applying the present silicone compound to cosmetics, ethanol and 2-propanol (isopropyl alcohol) are used to advantage. The addition reaction has no particular limitations on reaction conditions, but it is preferably carried out for 1 to 10 hours under reflux.

The present silicone compounds can be used for various purposes. In particular, they are suitable as materials for all of cosmetics applied to skin and hair. In mixing the silicone compound of formula (1) in a cosmetic material, the proportion thereof is preferably from 0.1 to 40% by weight to the total ingredients in the cosmetic material.

To the present cosmetic materials, the ingredients used in general cosmetic materials, such as water, powders, alcohols, water-soluble polymers, film-forming agents, unctuous agents, oil-soluble gelling agents, clay minerals modified with organic compounds, surfactants, resins, ultraviolet absorbents, moisture-holding agents, antiseptics, antimicrobial agents, perfume, salts, antioxidants, pH regulators, chelating agents, refrigerants, anti-inflammatory agents, skin beautifying components (a skin whitener, a cell activator, a rough dry skin improver, a blood circulation promoter, a skin astringent and an anti-seborrheic agent), vitamins, amino acids, nucleic acids, hormones and clathrate compounds, can be added so far as they have no adverse influence on the effects of the present invention.

The powders used in the present cosmetic materials may be any powders so far as they are known to be used in conventional cosmetic materials, irrespective of their shape (whether it is spherical, acicular or tabular), their size (whether it is on the order of fume, fine grain or pigment), and their structure (whether it is porous or nonporous). Specifically, the powders usable in the invention include inorganic powders, organic powders, surfactant metal salt powders, colored pigments, pearl pigments, metallic powder pigments and natural colors.

Examples of inorganic powders usable in the present cosmetic materials include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxide, boron nitride and silica.

Examples of organic powders usable in the present cosmetic materials include polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose powder, silk powder, nylon powder such as 12-nylon powder or 6-nylon powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, starch powder and lauroyl lysine powder.

Examples of surfactant metal salt powders (metal soap powders) usable in the present cosmetic materials include powders of zinc stearate, aluminum stearate, calcium stearate, magnesium stearate, zinc myristate, magensium myristate, zinc cetylphosphate, calcium cetylphosphate and zinc sodium cetylphosphate.

Examples of colored pigments usable in the present cosmetic materials include inorganic red pigments, such as iron oxide, iron hydroxide and iron titanate; inorganic brown pigments, such as γ-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powders combined with the inorganic pigments as recited above.

Examples of pearl pigments usable in the present cosmetic materials include titanium oxide-coated mica, bismuth oxychloride, titanium oxide-coated bismuth oxychloride, titanium oxide-coated talc, fish scales, and titanium oxide-coated colored mica; and examples of metallic powder pigments usable herein include aluminum powder, copper powder and stainless powder.

Examples of tar pigments which can be used in the present cosmetic materials include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and examples of natural pigments usable herein include powders of carminic acid, laccaic acid, carthamin, bradilin and crocin.

Additionally, the powders as recited above can be formed into complexes unless the resultant complexes weaken the effects of the invention, or those obtained by treating the powders as recited above with general oil, silicone oil, a fluorine-containing compound or a surfactant can also be used. Further, the powders as recited above can be used alone, or as a mixture of two or more thereof, if desired.

Examples of alcohols which can be used include lower alcohols, such as ethanol and isopropanol; sugar alcohols, such as sorbitol and maltose; and sterols, such as cholesterol, sitosterol, phytosterol and lanosterol.

Examples of water-soluble polymers which can be used include vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethyl acrylate and polyacrylamide; polyethyleneimines; cationic polymers; and inorganic water-soluble polymers, such as bentonite, aluminum magnesium silicate, montmorillonite, beidellite, nontronite, saponite, hectorite and silicic acid anhydride.

In these water-soluble polymers, film-forming agents, such as polyvinyl alcohol and polyvinyl pyrrolidine, are also included.

The unctuous agents in any of solid, semisolid and liquid states can be used in the present cosmetic materials so far as they have so far been used for general cosmetics. More specifically, not only natural animal and vegetable fats and oils but also semi-synthetic fats and oils can be mixed in the present cosmetic materials. Examples of unctuous agents usable herein include avocado oil, linseed oil, almond oil, Chinese wax, perilla oil, olive oil, cacao butter, kapok wax, kaya oil, carnauba wax, liver oil, candellila wax, beef tallow, beef foot fat, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, squalene, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, methyl ester of caster oil fatty acid, sunflower oil, grape oil, bayberry wax, jojoba oil, macadamia nut oil, beeds wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether, and egg yolk oil. Additionally, the term POE used herein stands for polyoxyethylene.

Examples of hydrocarbon oil which can be used herein include ozokerite, squalane, squalene, ceresine, paraffin, paraffin wax, liquid paraffin, pristane, polyisobutylene, microcrystalline wax and Vaseline; and examples of higher fatty acid which can be used include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohol which can be used herein include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oil which can be used herein include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid; and examples of glyceride oil which can be used herein include acetoglyceride, triisooctanoic acid glyride, triisostearic acid glyceride, triisopalmitic acid glyceride, monostearic acid glyceride, di-2-heptylundecanoic acid glyceride, trimyristic acid glyceride and myristic acid isostearic acid diglyceride.

Examples of silicone oils which can be used herein include organopolysiloxanes having from low to high viscosities, such as dimethylpolysiloxane, methylphenylpolysiloxane, methylhydrogenpolysiloxane and copolymer of dimethylsiloxane and methylphenylsiloxane; cyclic siloxanes, such as octamethylcyclotetrasiloxane, decamethylcyclopentasiloxane, dodecamethylcyclohexasiloxane and tetramethyltetrahydrogencyclotetrasiloxane; silicone rubber, such as gummy dimethylpolysiloxane having a high polymerization degree and gummy copolymer of dimethylsiloxane and methylphenylsiloxane; cyclosiloxane solutions of silicone rubber; trimethylsiloxysilicate; cyclosiloxane solutions of trimethylsiloxysilicate; higher alkoxy-modified silicones, such as stearoxysilicone; higher fatty acid-modified silicones; alkyl-modified silicones; amino-modified silicones; fluorine-modified silicones; and silicone resin solutions. And examples of a fluorine-containing unctuous agaent which can be used herein include perfluoropolyether, perfluorodecaline and perfluorooctane.

Examples of an oil-soluble gelling agent which can be used herein include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay. These gelling agents can be used alone or as a mixture of two or more thereof, if desired.

In addition to the ingredients recited above, the present cosmetic materials can contain surfactants. The surfactants used in the invention have no particular restriction, but they may be any of anionic, cationic, nonionic and amphoteric ones so long as they have hitherto been used in general cosmetics.

Examples of anionic surfactants usable herein include fatty acid soap, such as sodium stearate and triethanolamine palmitate; carboxylates, such as alkyl ether carboxylic acids and salts thereof, and amino acid-fatty acid condensates; sulfonates, such as alkane sulfonates, alkene sulfonates, sulfonated fatty acid esters, sulfonated fatty acid amides, and alkylsulfonate-formaldehyde condensate; sulfates, such as alkylsulfates, higher secondary alcohol sulfates, alkyl and aryl ether sulfates, fatty acid ether sulfates, fatty acid alkylolamide sulfates, ether sulfates, and Turkeky red oil; phosphates, such as alkyl phosphates, ether phosphates, alkyl aryl ether phosphates, and amide phosphates; and active agents of N-acylamino acid type.

Examples of cationic surfactants usable herein include amine salts, such as alkylamie salts, polyamines and aminoalcohol fatty acid derivatives; quaternary alkylammonium salts; quaternary arylammonium salts; pyridinium salts; and imidazolium salts.

Examples of nonionic surfactants usable herein include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxanes, organopolysiloxanes modified with both polyoxyalkylene and alkyl groups, alkanolamides, sugar ethers and sugar amides; and examples of amphoteric surfactants usable herein include betaines, aminocarboxylate and imdazoline derivatives.

Examples of an ultraviolet absorbent which can be added include ultraviolet absorbents of benzoic acid type such as p-aminobenzoic acid, those of anthranilic acid type such as methyl anthranilate, those of salicylic acid type such as methyl salicylate, those of succinic acid type such as octyl p-methoxysuccinate, those of benzophenone type such as 2,4-dihydroxybenzophenone, those of urocanic acid type such as ethyl urocanate, and those of dibenzoylmethane type such as 4-t-butyl-4'-methoxydibenzoylmethane.

Examples of a moisture-holding agent which can be added include glycerin, sorbitol, propylene glycol, dipropylene glycol, 1,3-butylene glycol, glucose, xylitol, maltitol, polyethylene glycol, hyaluronic acid, chondroitin sulfuric acid, pyrrolidone carboxylate, polyoxyethylene methylglycoside, and polyoxypropylene methylglycoside.

Examples of an antiseptic agent which can be added include alkyl p-hydroxybenzoates, benzoic acid, sodium benzoate, sorbic acid, potassium sorbate and phenoxyethanol; and examples of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorohexidine chloride, trichlorocarbanilide, photosensitizer and phenoxyethanol.

Examples of an antioxidant which can be added include tocopherol, butylhydroxyanisole, dibutylhydroxytoluene and phytic acid; examples of a pH regulator which can be added include lactic acid, citric acid, glycolic acid, succinic acid, tartaric acid, dl-malic acid, potassium carbonate, sodium hydrogen carbonate and ammonium hydrogen carbonate; examples of a chelating agent which can be added include alanine, sodium ethylenediaminetetraacetate, sodium polyphosphate, sodium metaphosphate and phosphoric acid; examples of a refrigerant which can be added include L-menthol and camphor; and examples of an antiinflammatory agent which can added include allantoin, glycyrrhizin, glycyrrhetinic acid, tranexamic acid and azulene.

Examples of skin-beautifying ingredients which can be added include whitening agents, such as placenta extract, arbutin, glutathione and Yukinoshita extract; cell activators, such as royal jelly, photosensitizer, cholesterol derivatives and calf blood extract; rough dry skin improvers; blood circulation improvers, such as nonylic acid vanillyl amide, benzyl nicotinate, $\beta$-butoxyethyl nicotinate, capsaicin, zingerone, cantharis tincture, ichtammol, caffeine, tannic acid, $\alpha$-borneol, tocopheryl nicotinate, inositol hexanicotinate, cyclandelate, cinnarizine, tolazoline, acetyl choline, verapamil, cepharanthin and $\gamma$-oryzanol; skin astringents, such as zinc oxide and tannic acid; and antiseborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as $\alpha$-tocopherol, $\beta$-tocopherol, $\gamma$-tocopherol, dl-$\alpha$-tocopheryl acetate, dl-$\alpha$-tocopheryl nicotinate and dl-$\alpha$-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an amino acid which can be added include glycine, valine, leucine, isoleucine, serine, threonine, phenylaranine, alginine, lysine, aspartic acid, glutamic acid, cystine, cysteine, methionine, and tryptophan; examples of a nucleic acid which can be added include deoxyribonucleic acid; and examples of hormone which can be added include estradiol and ethenyl estradiol.

The term "cosmetic material" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse and treatment. Additionally, the present cosmetic material may have any of liquid, emulsion, solid, paste, gel and spray forms, if desired.

The present invention will now be illustrated in greater detail by reference to the following examples and comparative examples. However, the invention should not be construed as being limited to these examples.

Additionally, the entire disclosure of all applications, patents and publications, cited above and below, and of corresponding Japanese application No. 11-216619, filed on Jul. 30, 1999, is hereby incorporated by reference.

EXAMPLE 1

In a reaction vessel, 714 parts by weight of organohydrogensiloxanes represented by the following average structural formula (8), 270 parts by weight of organopolysiloxanes represented by the following average structural formula (9) and 638 parts by weight of toluene were mixed, and thereto was added 2 parts by weight of a 0.5% toluene solution of chloroplatinic acid. Therein, reaction between those reactants was continued for 6 hours under reflux of the solvent.

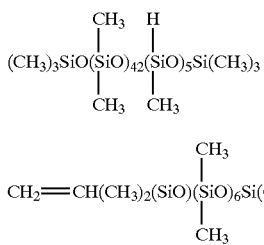

Thereto, 291 parts by weight of polyoxyalkylene compound represented by the following average structural formula (10) was further added and underwent reaction with the organohydrdogenpolysiloxanes:

After the reaction was continued for 6 hours under reflux of the solvent, the reaction mixture was heated under reduced pressure to distill off the solvent. To the residue, 200 parts by weight of ethanol was added first, and then 7.1 parts by weight of a 5 weight % aqueous solution of sodium hydroxide was added, thereby decomposing Si—H groups remaining unreacted, followed by neutralization with 0.9 parts by weight of concentrated hydrochloric acid. Further, the ally ether group of the polyoxyalkylene compound remaining unreacted was hydrolyzed by the addition of 147 parts by weight of a 0.01 N aqueous solution of hydrochloric acid, and then neutralization was carried out using 2.5 parts by weight of a 5 weight % aqueous solution of sodium hydrogen carbonate. The reaction product obtained was heated under reduced pressure to distill off the solvents, and then filtered off. Thus, organopolysiloxanes having the following average structural formula (11) (a silicone compound according to the invention) were obtained.

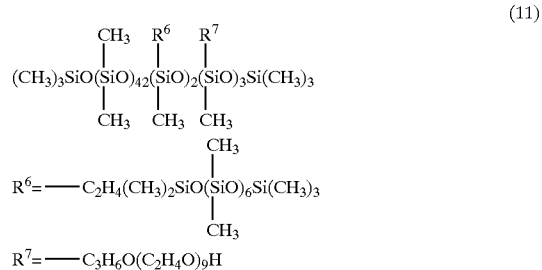

The product obtained was colorless transparent liquid, and it had a viscosity of 956 cs (at 25° C.) and a specific gravity of 1.002 (at 25° C.).

EXAMPLE 2

In a reaction vessel, 416 parts by weight of organohydrogensiloxanes represented by the following average structural formula (12), 952 parts by weight of the polyoxyalkylene compound represented by the foregoing average structural formula (10) and 600 parts by weight of isopropyl alcohol were mixed, and thereto was added 0.2 parts by weight of a 2% isopropyl alcohol solution of chloroplatinic acid. Therein, reaction between those reactants was continued for 6 hours under reflux of the solvent.

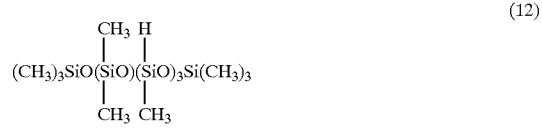

Thereto, 200 parts by weight of pentamethylvinyldisiloxane was further added and underwent reaction with the organohydrdogenpolysiloxanes.

After the reaction was continued for 6 hours under reflux of the solvent, the reaction mixture was admixed with 4.2 parts by weight of a 5 weight % aqueous solution of sodium hydroxide to decompose Si—H groups remaining unreacted, and then neutralized with 0.5 parts by weight of concentrated hydrochloric acid. Further, the ally ether group of the polyoxyalkylene compound remaining unreacted was hydrolyzed by the addition of 217 parts by weight of a 0.01 N aqueous solution of hydrochloric acid, and then neutralization was carried out using 3.6 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (13) (a silicone compound according to the invention) were obtained.

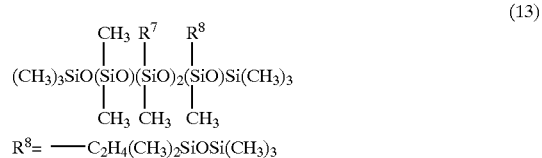

The product obtained was colorless transparent liquid, and it had a viscosity of 180 cs (at 25° C.) and a specific gravity of 1.044 (at 25° C.)

EXAMPLE 3

In a reaction vessel, 652 parts by weight of organohydrogensiloxanes represented by the following average structural formula (14), 286 parts by weight of the polyoxyalkylene compound represented by the foregoing average structural formula (10) and 600 parts by weight of isopropyl alcohol were mixed, and thereto was added 0.2 parts by weight of a 2% isopropyl alcohol solution of chloroplatinic acid. Therein, reaction between those reactants was continued for 6 hours under reflux of the solvent.

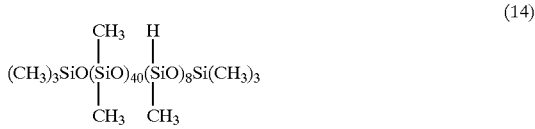

(14)

Thereto, 270 parts by weight of the organopolysiloxanes represented by the foregoing average structural formula (9) was further added and underwent reaction with the organohydrdogenpolysiloxanes.

After the reaction was continued for 6 hours under reflux of the solvent, 111 parts by weight of 1-dodecene was added, and heated for 3 hours under reflux to complete the reaction. Then, the reaction mixture was admixed with 6.5 parts by weight of a 5 weight % aqueous solution of sodium hydroxide to decompose Si—H groups remaining unreacted, and then neutralized with 0.8 parts by weight of concentrated hydrochloric acid. Further, the ally ether group of the polyoxyalkylene compound remaining unreacted was hydrolyzed by the addition of 192 parts by weight of a 0.01 N aqueous solution of hydrochloric acid, and then neutralization was carried out using 3.2 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (15) (a silicone compound according to the invention) were obtained.

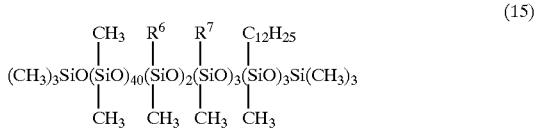

(15)

The product obtained was colorless transparent liquid, and it had a viscosity of 1,130 cs (at 25° C.) and a specific gravity of 0.992 (at 25° C.).

EXAMPLE 4

In a reaction vessel, 838 parts by weight of the organohydrogenpolysiloxanes represented by the foregoing average structural formula (14) and 1,000 parts by weight of toluene were mixed, and thereto 0.2 parts by weight of a 2 weight % isopropyl alcohol solution of chloroplatinic acid was added. Further thereto, 338 parts by weight of the organopolysiloxanes represented by the foregoing average structural formula (9) was added dropwise, and underwent reaction for 6 hours under reflux of the solvent.

Then, the solvent was distilled off, and the resultant reaction mixture was admixed with 600 parts by weight of isopropyl alcohol and 0.2 parts by weight of a 2 weight % isopropyl alcohol solution of chloroplatinic acid. Thereto, the polyoxyalkylene compound represented by the foregoing average structural formula (10) was added dropwise and underwent reaction for 6 hours under reflux of the solvent. Further thereto, 216 parts by weight of allyl cetyl ether was added, and heated for 3 hours under reflux to complete the reaction. Then, the reaction mixture was admixed with 8.4 parts by weight of a 5 weight % aqueous solution of sodium hydroxide to decompose Si—H groups remaining unreacted, and then neutralized with 1.1 parts by weight of concentrated hydrochloric acid. Further, the ally ether group of the polyoxyalkylene compound remaining unreacted was hydrolyzed by the addition of 235 parts by weight of a 0.01 N aqueous solution of hydrochloric acid, and then neutralization was carried out using 3.9 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (16) (a silicone compound according to the invention) were obtained.

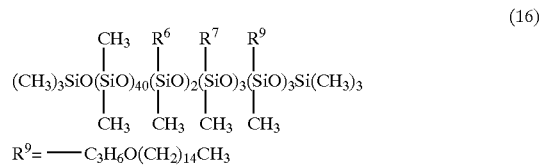

(16)

The product obtained was transparent light-brown liquid, and it had a viscosity of 530 cs (at 25° C.) and a specific gravity of 0.985 (at 25° C.).

EXAMPLE 5

In a reaction vessel, 838 parts by weight of the organohydrogenpolysiloxanes represented by the foregoing average structural formula (14) and 600 parts by weight of isopropyl alcohol were mixed, and thereto 0.2 parts by weight of a 2 weight % isopropyl alcohol solution of chloroplatinic acid was added. Further thereto, 338 parts by weight of the organopolysiloxanes represented by the foregoing average structural formula (9) was added dropwise and underwent reaction for 3 hours under reflux of the solvent. Furthermore thereto, 357 parts by weight of the polyoxyalkylene compound represented by the foregoing average structural formula (10) was added dropwise and underwent reaction for 3 hours.

In addition to those reactants, 424 parts by weight of oleylpolyoxypropylene(3) allyl ether RG-1252 (trade name, a product of SANYO CHEMICAL INDUSTRIES, LTD.) was added, and heated for 3 hours under reflux to complete the reaction. Then, the reaction mixture was admixed with 8.4 parts by weight of a 5 weight % aqueous solution of sodium hydroxide to decompose Si—H groups remaining unreacted, and then neutralized with 1.1 parts by weight of concentrated hydrochloric acid. Further, the ally ether groups of the polyoxyalkylene compounds remaining unreacted were hydrolyzed by the addition of 255 parts by weight of a 0.01 N aqueous solution of hydrochloric acid, and then neutralization was carried out using 4.3 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (17) (a silicone compound according to the invention) were obtained.

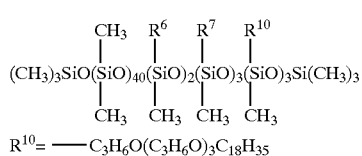

The product obtained was transparent light-brown liquid, and it had a viscosity of 340 cs (at 25° C.) and a specific gravity of 0.981 (at 25° C.).

EXAMPLE 6

In a reaction vessel, 416 parts by weight of the organohydrogenpolysiloxanes represented by the foregoing average structural formula (12), 952 parts by weight of the polyoxyalkylene compound represented by the foregoing average structural formula (10) and 600 parts by weight of isopropyl alcohol were mixed, and thereto 0.2 parts by weight of a 2 weight % isopropyl alcohol solution of chloroplatinic acid was added. Therein, reaction was run for 6 hours under reflux of the solvent. Thereto, 107 parts by weight of pentamethylvinyldisiloxane was further added, and reaction was continued.

After the reaction was continued for 6 hours under reflux of the solvent, 67 parts by weight of 1-dodecene was further added, and heated for 3 hours under reflux to complete the reaction. Then, the reaction mixture was admixed with 4.2 parts by weight of a 5 weight % aqueous solution of sodium hydroxide to decompose Si—H groups remaining unreacted, and then neutralized with 0.5 parts by weight of concentrated hydrochloric acid. Further, the ally ether group of the polyoxyalkylene compound remaining unreacted was hydrolyzed by the addition of 214 parts by weight of a 0.01 N aqueous solution of hydrochloric acid, and then neutralization was carried out using 3.6 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (18) (a silicone compound according to the invention) were obtained.

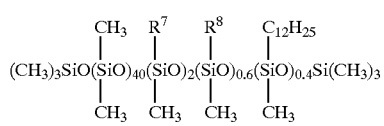

The product obtained was transparent colorless liquid, and it had a viscosity of 380 cs (at 25° C.) and a specific gravity of 1.044 (at 25° C.)

EXAMPLE 7

In a reaction vessel, 585 parts by weight of organohydrogenpolysiloxanes represented by the following average structural formula (19), 333 parts by weight of the polyoxyalkylene compound represented by the foregoing average structural formula (10) and 600 parts by weight of isopropyl alcohol were mixed, and thereto 0.2 parts by weight of a 2 weight % isopropyl alcohol solution of chloroplatinic acid was added. Therein, reaction was run for 6 hours under reflux of the solvent.

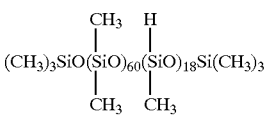

Thereto, 270 parts by weight of the organopolysiloxanes represented by the foregoing average structural formula (9) were further added, and reaction was continued. After the reaction was continued for 6 hours under reflux of the solvent, 129 parts by weight of 1-dodecene was further added, and heated for 3 hours under reflux to complete the reaction. Then, the reaction mixture was admixed with 5.9 parts by weight of a 5 weight % aqueous solution of sodium hydroxide to decompose Si—H groups remaining unreacted, and then neutralized with 0.7 parts by weight of concentrated hydrochloric acid. Further, the ally ether group of the polyoxyalkylene compound remaining unreacted was hydrolyzed by the addition of 192 parts by weight of a 0.01 N aqueous solution of hydrochloric acid, and then neutralization was carried out using 3.2 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (20) (a silicone compound according to the invention) were obtained.

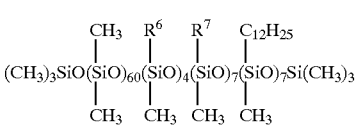

The product obtained was transparent colorless liquid, and it had a viscosity of 5,000 cs (at 25° C.) and a specific gravity of 0.991 (at 25° C.).

EXAMPLE 8

In a reaction vessel, 585 parts by weight of the organohydrogenpolysiloxanes represented by the foregoing average structural formula (19), 381 parts by weight of the polyoxyalkylene compound represented by the foregoing average structural formula (10) and 600 parts by weight of isopropyl alcohol were mixed, and thereto 0.2 parts by weight of a 2 weight % isopropyl alcohol solution of chloroplatinic acid was added. Therein, reaction was run for 6 hours under reflux of the solvent.

Thereto, 556 parts by weight of organopolysiloxanes represented by the following average structural formula (21) and 283 parts by weight of oleylpolyoxypropylene(3) allyl ether RG-1252 (trade name, a product of SANYO CHEMI CAL INDUSTRIES, LTD.) were further added dropwise, and reaction was continued.

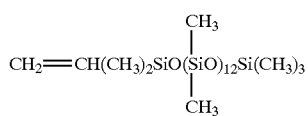
(21)

After the reaction was run for 6 hours, the reaction mixture was cooled, and then admixed with 5.8 parts by weight of a 5 weight % aqueous solution of sodium hydroxide to decompose Si—H groups remaining unreacted, and neutralized with 1.1 parts by weight of concentrated hydrochloric acid. Further, the ally ether group of the polyoxyalkylene compound remaining unreacted was hydrolyzed by the addition of 240 parts by weight of a 0.01 N aqueous solution of hydrochloric acid, and then neutralization was carried out using 4.0 parts by weight of a 5 weight % aqueous solution of sodium hydrogen carbonate.

The reaction product obtained was heated under reduced pressure to distill off the solvents, and then filtered off. Thus, organopolysiloxanes having the following average structural formula (22) (a silicone compound according to the invention) were obtained.

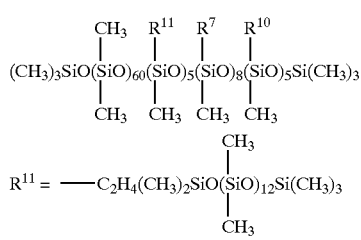
(22)

The product obtained was transparent colorless liquid, and it had a viscosity of 1,840 cs (at 25° C.) and a specific gravity of 0.991 (at 25° C.).

EXAMPLE 9

In a reaction vessel, 58.5 parts by weight of the organohydrogenpolysiloxanes represented by the foregoing average structural formula (19), 261 parts by weight of organopolysiloxanes represented by the following average structural formula (23) and 285 parts by weight of polyoxyalkylene compound represented by the following average structural formula (24) and 1,000 parts by weight of isopropyl alcohol were mixed, and thereto 0.2 parts by weight of a 2 weight % isopropyl alcohol solution of chloroplatinic acid was added. Therein, reaction was run for 6 hours under reflux of the solvent.

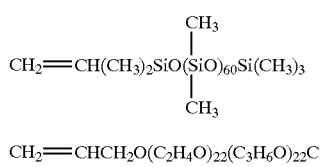
(23)

(24)

The resultant reaction mixture was admixed with 0.59 parts by weight of a 5 weight % aqueous solution of sodium hydroxide to decompose Si—H groups remaining unreacted, and neutralized with 0.1 parts by weight of concentrated hydrochloric acid. Further, the ally ether group of the polyoxyalkylene compound remaining unreacted was hydrolyzed by the addition of 160 parts by weight of a 0.01 N aqueous solution of hydrochloric acid, and then neutralization was carried out using 2.7 parts by weight of a 5 weight % aqueous solution of sodium hydrogen carbonate.

The reaction product obtained was heated under reduced pressure to distill off the solvents to yield a transparent organopolysiloxane gel having the following average structural formula (25) (a silicone compound according to the invention).

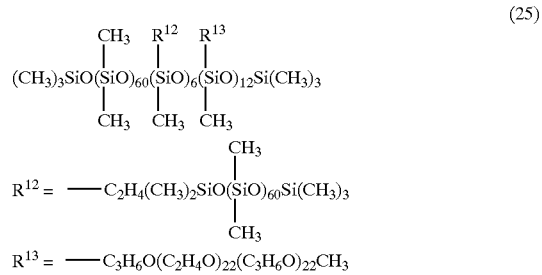
(25)

EXAMPLE 10

In a reaction vessel, 380 parts by weight of the polyoxyalkylene compound represented by the foregoing average structural formula (10), 222 parts by weight of the organopolysiloxanes represented by the foregoing average structural formula (21) and 600 parts by weight of isopropyl alcohol were mixed, and thereto 0.2 parts by weight of a 2 weight % of isopropyl alcohol solution of chloroplatinic acid was added. Thereto, 546 parts by weight of organohydrogensiloxanes represented by the following average structural formula (26) was added dropwise to undergo reaction under reflux of the solvent.

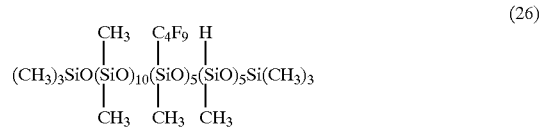
(26)

To the resultant reaction mixture, 5.5 parts by weight of a 5 weight % aqueous solution of sodium hydroxide was added to decompose Si—H groups remaining unreacted, followed by neutralization with 0.7 parts by weight of concentrated hydrochloric acid.

Further, the ally ether group of the polyoxyalkylene compound remaining unreacted was hydrolyzed by the addition of 175 parts by weight of a 0.01 N aqueous solution of hydrochloric acid, and then neutralization was carried out using 2.9 parts by weight of a 5 weight % aqueous solution of sodium hydrogen carbonate.

The reaction product obtained was heated under reduced pressure to distill off the solvents to yield a silicone com pound represented by the following average structural formula (27).

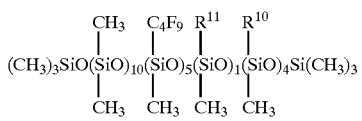
(27)

The product obtained was a transparent colorless liquid, and had a viscosity of 910 cs (25°) and a specific gravity of 1.131 (25°).

EXAMPLE 11

Eyeliner containing the following ingredients was prepared in accordance with the process described below:

| | Ingredients | Amount mixed (wt %) |
|---|---|---|
| 1. | Octamethylcyclotetrasiloxane | the rest |
| 2. | Silicone compound of Example 8 | 3.0 |
| 3. | Silicone resin (*1) | 15.0 |
| 4. | Dioctadecyldimethylammonium salt-modified montmorillonite | 3.0 |
| 5. | Silicone-treated iron oxide black (*2) | 10.0 |
| 6. | 1,3-Butylene glycol | 5.0 |
| 7. | Sodium dehydroacetate | proper |
| 8. | Antiseptic | proper |
| 9. | Perfume | proper |
| 10. | Purified water | 10 |

(*1) 50% Decamethylcyclopentasiloxane solution of netted silicone compound having a [Me$_3$SiO$_{1/2}$]/[SiO$_2$] ratio of 0.8
(*2) Iron oxide black powder rendered hydrophobic by treatment with methylhydrogenpolysiloxne added thereto in a proportion of 2 wt % and subsequent heating.

[Preparation Process]
A: The ingredients 1 to 4 were mixed together, and thereto the ingredient 5 was further added. These ingredients were dispersed homogeneously.
B: The ingredients 6, 7, 8 and 10 were mixed.
C: The mixture obtained in the step B was added little by little to the dispersion obtained in the step A to make an emulsion, and then the ingredient 9 was added to the emulsion.

The thus prepared eyeliner spread smoothly, and so the users thereof were able to outline the eyes easily. Further, this eyeliner had no tacky feel, but provided cool and dry feelings to the users. In addition, it was confirmed that the present eyeliner caused no change in quality by temperature and aging, it had very excellent usability and stability, and the duration of its effect was very long because of its high resistance to water and sweat and the like.

EXAMPLE 12

Suntan milk constituted of the following ingredients was prepared in accordance with the process described below:

| | Ingredients | Amount mixed (wt %) |
|---|---|---|
| 1. | Emulsifier composition (*1) | 6.0 |
| 2. | Dimethylpolysiloxane (20 cs) | 49.0 |
| 3. | 1,3-Butylene glycol | 5.0 |
| 4. | Sodium dehydroacetate | proper |
| 5. | Antioxidant | proper |
| 6. | Antiseptic | proper |
| 7. | Perfume | proper |
| 8. | Purified water | the rest |

(*1) Emulsifier composition constituted of:
  a. 10.0 parts by weight of a silicone compound synthesized in Example 1
  b. 10.0 parts by weight of dioctadecyldimethylammonium salt-modified montmorillonite,
  c. 40.0 parts by weight of ethanol.

[Preparation Process]
A: The ingredient a was dissolved in the ingredient c, and thereto the ingredient b was added.
B: The admixture obtained in the step A was stirred for 1 hour with a dispersion mill, and then the ethanol was removed therefrom with an evaporator.
C: The residue obtained in the step B was dried at 50° C. for twenty-four hours to prepare an emulsifier composition as the ingredient 1.
D: The ingredient 1 was mixed with the ingredient 2.
E: The ingredients 3 to 6 and 8 were mixed homogeneously.
F: To the mixture obtained in the step D with stirring, the homogeneous mixture obtained in the step E was added little by little to make an emulsion, and then the ingredient 7 was added to the emulsion.

The thus prepared suntan milk had a fine texture, spread smoothly and lightly, had neither tacky nor oily feel, and gave moist and fresh feel to the users' skin. Further, this milk had high resistance to water and the effect thereof kept for a long time. In addition, it was confirmed that the present suntan milk caused no change in quality by temperature changes and elapsed time, namely, it had very excellent stability.

EXAMPLE 13

Suntan cream constituted of the following ingredients was prepared in accordance with the process described below:

| | Ingredients | Amount mixed (wt %) |
|---|---|---|
| 1. | Decamemthylcyclopentasiloxane | 15.0 |
| 2. | Dimethylpolysiloxane (100 cs) | 5.0 |
| 3. | Silicone wax | 0.5 |
| 4. | Silicone compound of Example 5 | 6.0 |
| 5. | Palmitic acid | 0.2 |
| 6. | Dimethyloctylparaaminobenzoic acid | 0.5 |
| 7. | 4-t-Butyl-4'-methoxy-dibenzoylmethane | 0.5 |
| 8. | Kaolin | 0.5 |
| 9. | Iron oxide red | 0.2 |
| 10. | Iron oxide yellow | 0.3 |
| 11. | Iron oxide black | 0.1 |
| 12. | Titanium dioxide-coated mica | 1.0 |
| 13. | Sodium L-glutamate | 3.0 |
| 14. | 1,3-Butylene glycol | 5.0 |
| 15. | Dioctadecyldimethylammonium chloride | 0.1 |
| 16. | Antioxidant | proper |
| 17. | Antiseptic | proper |
| 18. | Perfume | proper |
| 19. | Purified water | the rest |

[Preparation Process]
A: The ingredients 1 to 7, 16 and 17 were mixed and heated to prepare a solution.

B: The ingredient 15 and a part of the ingredient 19 were mixed and heated with stirring, and thereto the ingredients 8 to 12 were added, followed by undergoing dispersion treatment.

C: The ingredients 13 and 14 and the rest of the ingredient 19 were made into a homogeneous solution, and mixed with the dispersion obtained in the step B.

D: To the solution prepared in the step A with stirring, the mixture obtained in the step C was added little by little to prepare an emulsion. The emulsion prepared was cooled, and thereto the ingredient 18 was added.

The thus prepared suntan cream had a fine texture, spread smoothly and lightly, had neither tacky nor oily feel, and gave moist and fresh feel to the users' skin. Further, this cream gave a feeling of good fit to the users and the effect thereof kept for a long time. In addition, it was confirmed that the present suntan cream caused neither separation of ingredients nor flocculation of powders by change in temperature and storage, namely, it had very excellent stability.

EXAMPLE 14

The following ingredients were mixed together, and made into foundation in accordance with the process described below:

| | Ingredients | Amount mixed (wt %) |
|---|---|---|
| 1. | Decamethylcyclopentasiloxane | 45.0 |
| 2. | Dimethylpolysiloxane (6 cs) | 5.0 |
| 3. | Silicone compound of Example 1 | 1.5 |
| 4. | Silicone compound of Example 3 | 0.5 |
| 5. | Octadecyldimethylbenzylammonium salt -modified montmorillonite | 4.0 |
| 6. | Titanium dioxide treated so as to have hydrophobicity (*1) | 10.0 |
| 7. | Talc treated so as to have hydrophobicity (*1) | 6.0 |
| 8. | Mica treated so as to have hydrophobicity (*1) | 6.0 |
| 9. | Ion oxide red treated so as to have hydrophobicity (*1) | 1.6 |
| 10. | Iron oxide yellow treated so as to have hydrophobicity (*1) | 0.7 |
| 11. | Iron oxide black treated so as to have hydrophobicity (*1) | 0.2 |
| 12. | Dipropylene glycol | 5.0 |
| 13. | Methyl paraoxybenzoate | 0.3 |
| 14. | 2-Amino-2-methyl-1,3-propanediol | 0.2 |
| 15. | Hydrochloric acid | 0.1 |
| 16. | Perfume | proper |
| 17. | Purified water | the rest |

(*1) Each powder was rendered hydrophobic by treatment with methylhydrogenpolysiloxne added thereto in a proportion of 2 wt % and subsequent heating.

[Preparation Process]

A: The ingredients 1 to 5 were mixed together under heating, and thereto the ingredients 6 to 11 were added. Then, these mixed ingredients were made homogeneous.

B: The ingredients 12 to 15 and 17 were mixed together, and made into a solution by heating (the pH of this aqueous solution was 9.0).

C: The solution obtained in the step B was added little by little to the homogeneous dispersion obtained in the step A with stirring, thereby making an emulsion. After the emulsion was cooled, the ingredient 16 was added thereto.

The foundation thus prepared had fine texture, spread lightly and smoothly, had neither oily nor tacky feel, and rendered the skin moist, youthful and refreshing. Further, it was confirmed that the present foundation ensured durable makeup effect, and besides, caused no change by temperature changes and elapsed time, namely it had very high stability.

EXAMPLE 15

Hair cream constituted of the following ingredients was prepared in accordance with the process described below:

| | Ingredients | Amount mixed (wt %) |
|---|---|---|
| 1. | Decamethylcyclopentasiloxane | 10.0 |
| 2. | Methylphenylpolysiloxane | 5.0 |
| 3. | Squalane | 4.0 |
| 4. | Silicone resin (*1) | 1.0 |
| 5. | Glyceryl dioleate | 2.0 |
| 6. | Silicone compound of Example 4 | 4.0 |
| 7. | Sodium sorbitol sulfate | 2.0 |
| 8. | Sodium chontroitin sulfate | 1.0 |
| 9. | Sodium hyaluronate | 0.5 |
| 10 | Propylene glycol | 3.0 |
| 11. | Antiseptic | 1.5 |
| 12. | Vitamin E acetate | 0.1 |
| 13. | Antioxidant | proper |
| 14. | Perfume | proper |
| 15. | Purified water | the rest |

(*1) 50% Decamethylcyclopentasiloxane solution of netted silicone compound having a $[Me_3SiO_{1/2}]/[SiO_2]$ ratio of 0.8

[Preparation Process]

A: The ingredients 1 to 6, 11 and 12 were mixed under heating.

B: The ingredients 7 to 10 and 15 were mixed under heating.

C: To the mixture obtained in the step A with stirring, the mixture obtained in the step B was added little by little to make an emulsion. The emulsion was cooled, and then admixed with the ingredient 14.

The thus prepared hair cream spread smoothly, had neither tacky nor oily feel, and gave a moist, fresh and youthful feel to the users' hair. Further, it was confirmed that this hair cream kept its effect for a long time because of its good water resistance, water repellency and perspiration resistance, and besides, caused no change by temperature changes and elapsed time, namely it had very high stability.

EXAMPLE 16

Eye wrinkle cream constituted of the following ingredients was prepared in accordance with the process described below:

| | Ingredients | Amount mixed (wt %) |
|---|---|---|
| 1. | Decamethylcyclopentasiloxane | 20.0 |
| 2. | Trimethylsiloxysilicate | 5.0 |
| 3. | Silicone compound of Example 3 | 5.0 |
| 4. | Sodium chondroitin sulfate | 2.0 |
| 5. | Sodium lactate | 1.0 |
| 6. | Glycerin | 50.0 |
| 7. | Antiseptic | proper |
| 8. | Antioxidant | proper |
| 9. | Perfume | proper |
| 10. | Purified water | the rest |

[Preparation Process]

A: The ingredients 1 to 3 and 8 were mixed under heating.

B: The ingredients 4 to 7 and 10 were mixed and dissolved under heating.

C: To the mixture obtained in the step A with stirring, the solution obtained in the step B was added little by little to make an emulsion. The emulsion was cooled, and then admixed with the ingredient 9.

The thus prepared eye wrinkle cream spread smoothly, had neither tacky nor oily feel, and gave moist, fresh and youthful feelings to the users. Further, it was confirmed that this cream kept its effect for a long time, and besides, caused no change in quality by temperature changes and elapsed time, namely it had very high stability.

EXAMPLE 17

Cream constituted of the following ingredients was prepared in accordance with the process described below:

|     | Ingredients | Amount mixed (wt %) |
| --- | --- | --- |
| 1.  | Decamethylcyclopentasiloxane | 20.0 |
| 2.  | Glyceryl trioctanoate | 10.0 |
| 3.  | Silicone compound of Example 3 | 4.0 |
| 4.  | Phenyldimethylstearylammonium chlorride | 1.0 |
| 5.  | Dipropylene glycol | 10.0 |
| 6.  | Maltitol | 10.0 |
| 7.  | Saponite | 1.5 |
| 8.  | Antiseptic | proper |
| 9.  | Perfume | proper |
| 10. | Purified water | the rest |

[Preparation Process]
A: The ingredients 1 to 4 and 8 were mixed under heating.
B: The ingredients 5 to 7 and 10 were mixed and dissolved under heating.
C: To the mixture obtained in the step A with stirring, the solution obtained in the step B was added little by little to make an emulsion. The emulsion was cooled, and then admixed with the ingredient 9.

The thus prepared cream spread smoothly, had neither tacky nor oily feel, and gave a moist, fresh and youthful feel to the users' skin. Further, it was confirmed that this cream ensured a durable makeup effect, and besides, caused no change in quality by temperature changes and elapsed time, namely it had very high stability.

EXAMPLE 18

Hand cream constituted of the following ingredients was prepared in accordance with the process described below:

|     | Ingredients | Amount mixed (wt %) |
| --- | --- | --- |
| 1.  | Decamethylcyclopentasiloxane | 12.0 |
| 2.  | Liquid paraffin | 10.0 |
| 3.  | Organic silicone resin (*1) | 5.0 |
| 4.  | Silicone compound of Example 4 | 4.0 |
| 5.  | Distearyldimethylammonium chloride | 0.8 |
| 6.  | Vitamin E acetate | 0.1 |
| 7.  | Polyethylene glycol 4000 | 1.0 |
| 8.  | Glycerin | 10.0 |
| 9.  | Aluminum magnesium silicate | 1.2 |
| 10. | Antiseptic | proper |
| 11. | Perfume | proper |
| 12. | Purified water | the rest |

(*1) Silicone resin having an average formula $(CH_3)_{1.60}SiO_{1.20}$ and a molecular weight of 3,000

[Preparation Process]
A: The ingredients 1 to 6 and 10 were mixed under heating.
B: The ingredients 7 to 9 and 12 were mixed and dissolved under heating.
C: To the mixture obtained in the step A with stirring, the solution obtained in the step B was added little by little to make an emulsion. The emulsion was cooled, and then admixed with the ingredient 11.

The thus prepared hand cream spread smoothly, had neither tacky nor oily feel, and gave a moist, fresh and youthful feel to the users' hand. Further, it was confirmed that this cream kept its effect for a long time because of its good water resistance and water repellency, and besides, caused no change in quality by temperature changes and elapsed time, namely it had very high stability.

EXAMPLE 19

Sunscreen cream constituted of the following ingredients was prepared in accordance with the process described below:

|     | Ingredients | Amount mixed (wt %) |
| --- | --- | --- |
| 1.  | Decamethylcyclopentasiloxane | 20.0 |
| 2.  | Liquid paraffin | 10.0 |
| 3.  | Silicone compound of Example 5 | 4.0 |
| 4.  | 4-t-Butyl-4'-methoxydibenzoylmethane | 7.0 |
| 5.  | Distearyldimethylammonium chloride | 0.8 |
| 6.  | Vitamin E acetate | 0.1 |
| 7.  | Ethanol | 1.0 |
| 8.  | Aluminum magnesium silicate | 1.2 |
| 9.  | Antiseptic | proper |
| 10. | Perfume | proper |
| 11. | Purified water | the rest |

[Preparation Process]
A: The ingredients 1 to 6 and 9 were mixed together under heating.
B: The ingredients 7, 8 and 11 were heated, and made into a homogeneous dispersion.
C: The dispersion obtained in the step B was added little by little to the mixture obtained in the step A with stirring, thereby making an emulsion. After the emulsion was cooled, the ingredient 10 was added thereto.

The sunscreen cream thus prepared had fine texture, and spread smoothly to give a moist and fresh feel to the cream-applied skin. In addition, the cream-applied skin had no tackiness, and so it had no adhesion of sand. Therefore, it can be said that this sunscreen cream had excellent usability. Further, it was confirmed that this sunscreen cream ensured durable makeup effect and kept its UV protection effect for a long time, and besides, caused no change in quality by temperature changes and elapsed time, namely it had very high stability.

EXAMPLE 20

Cream constituted of the following ingredients was prepared in accordance with the process described below:

|     | Ingredients | Amount mixed (wt %) |
| --- | --- | --- |
| 1.  | Decamethylcyclopentasiloxane | 10.0 |
| 2.  | Dimethylpolysiloxane (6 cs) | 5.0 |
| 3.  | Liquid paraffin | 5.0 |
| 4.  | Silicone compound of Example 8 | 5.0 |
| 5.  | Sodium citrate | 2.0 |
| 6.  | 1,3-Butylene glycol | 5.0 |
| 7.  | Antiseptic | proper |

-continued

| | Ingredients | Amount mixed (wt %) |
|---|---|---|
| 8. | Perfume | proper |
| 9. | Purified water | the rest |

[Preparation Process]
A: The ingredients 1 to 4 were mixed under heating.
B: The ingredients 5 to 7 and 9 were mixed and dissolved under heating.
C: To the mixture obtained in the step A with stirring, the solution obtained in the step B was added little by little to make an emulsion. The emulsion was cooled, and then admixed with the ingredient 8.

The thus prepared cream spread smoothly, had neither tacky nor oily feel, and gave a moist, youthful and fresh feel to the users' skin. Further, it was confirmed that this cream had good water resistance and water repellency and ensured a durable makeup effect, and besides, caused no change in quality by temperature changes and elapsed time, namely it had very high stability.

EXAMPLE 21

Eye shadow constituted of the following ingredients was prepared in accordance with the process described below:

| | Ingredients | Amount mixed (wt %) |
|---|---|---|
| 1. | Decamethylcyclopentasiloxane | 15.0 |
| 2. | Dimethylpolysiloxane (6 cs) | 10.0 |
| 3. | Silicone compound of Example 9 | 2.0 |
| 4. | PEG(10) lauryl ether | 0.5 |
| 5. | Silicone-treated chromium oxide (*1) | 6.2 |
| 6. | Silicone-treated ultramarine blue (*1) | 4.0 |
| 7. | Silicone-treated titanium-coated mica (*1) | 6.0 |
| 8. | Sodium chloride | 2.0 |
| 9. | Propylene glycol | 8.0 |
| 10. | Antiseptic | proper |
| 11. | Perfume | proper |
| 12. | Purified water | the rest |

(*1) The treatment with silicone was effected by adding methylhydrogenpolysiloxane to each powder in a proportion of 3 wt % to the powder and then subjecting the powder to heat treatment.

[Preparation Process]
A: The ingredients 1 to 4 were mixed together, and thereto the ingredients 5 to 7 were further added. These ingredients were dispersed homogeneously.
B: The ingredients 8 to 10 and 12 were mixed to make a homogeneous solution.
C: The solution obtained in the step B was added little by little to the dispersion obtained in the step A with stirring, thereby making an emulsion, and then the ingredient 11 was added to the emulsion.

The thus prepared eye shadow spread smoothly, had neither oily nor powdery feel, and provided moist and refreshing feelings to the users. Further, it was confirmed that the present eye shadow ensured durable makeup effect because of its high water-resistance, water repellency and sweat resistance, and besides, caused no change in quality by temperature changes and elapsed time, namely it had very high stability.

EXAMPLE 22

Eyeliner constituted of the following ingredients was prepared in accordance with the process described below:

| | Ingredients | Amount mixed (wt %) |
|---|---|---|
| 1. | Decamethylcyclopentasiloxane | 22.0 |
| 2. | Dimethylpolysiloxane (6 cs) | 5.0 |
| 3. | Jojoba oil | 2.0 |
| 4. | Silicone compound of Example 5 | 1.0 |
| 5. | Silicone-treated iron oxide black (*1) | 20.0 |
| 6. | Ethanol | 5.0 |
| 7. | Antiseptic | proper |
| 8. | Purified water | the rest |

(*1) Iron oxide black was treated by addition of methylhydrogenpolysiloxne in a proportion of 2 wt % to the iron oxide black and heat treatment subsequent thereto.

[Preparation Process]
A: The ingredients 1 to 4 were warmed and mixed together, and hereto the ingredient 5 was further added. These ingredients were dispersed homogeneously.
B: The ingredients 6 to 8 were mixed and warmed to make a solution.
C: The solution obtained in the step B was added little by little to the dispersion obtained in the step A with stirring, thereby making an emulsion.

The thus prepared eyeliner spread smoothly, had neither oily nor powdery feel, and provided moist and refreshing feelings to the users. Further, it was confirmed that the present eyeliner ensured durable makeup effect because of its high water-resistance, water repellency and sweat resistance, and besides, caused no change in quality by temperature changes and elapsed time, namely it had very high stability.

EXAMPLE 23

Lip cream constituted of the following ingredients was prepared in accordance with the process described below:

| | Ingredients | Amount mixed (wt %) |
|---|---|---|
| 1. | Decamethylcyclopentasiloxane | 40.0 |
| 2. | Isoparaffin (b. pt. 155° C.) | 10.0 |
| 3. | Squalane | 10.0 |
| 4. | Lanolin | 2.0 |
| 5. | Trimethylsiloxysilicate | 3.0 |
| 6. | Microcrystalline wax | 3.0 |
| 7. | Silicone compound of Example 3 | 3.0 |
| 8. | Lauroylglutamic acid dibutylamide | 5.0 |
| 9. | Sodium lactate | 0.3 |
| 10. | Sodium L-glutamic acid | 0.3 |
| 11. | Sodium hyaluronate | 0.1 |
| 12. | Sorbitol | 0.5 |
| 13. | Glycerin | 5.0 |
| 14. | Red No. 202 | proper |
| 15. | Menthol | proper |
| 16. | Antiseptic | proper |
| 17. | Perfume | proper |
| 18. | Purified water | the rest |

[Preparation Process]
A: The ingredients 1 to 8 were mixed under heating.
B: The ingredients 9 to 16 and 18 were mixed and dissolved under heating.
C: The solution obtained in the step B was added little by little to the mixture obtained in the step A with stirring to make an emulsion. The emulsion was admixed with the ingredient 17, and then charged into capsules.

The thus prepared water-in-oil solid-state lip cream spread smoothly, had neither tacky nor oily feel, gave moist and fresh feelings to the users, and besides, it ensured durable makeup effect and had high treatment effect. Further, it was confirmed that the present lip cream caused no change in quality by temperature changes and elapsed time, namely it had very high stability.

EXAMPLE 24

Liquid emulsive foundation constituted of the following ingredients was prepared in accordance with the process described below:

| | Ingredients | Amount mixed (wt %) |
|---|---|---|
| 1. | Dimethylpolysiloxane (6 cs) | 5.0 |
| 2. | Decamethylcyclopentasiloxane | 15.0 |
| 3. | Squalane | 4.0 |
| 4. | Neopentyl glycol dioctanoate | 3.0 |
| 5. | Miristic acid isostearic acid diglyceride | 2.0 |
| 6. | α-Monoisostearyl glyceryl ether | 1.0 |
| 7. | Silicone compound of Example 3 | 1.0 |
| 8. | Aluminum distearate | 0.2 |
| 9. | Titanium dioxide treated so as to have hydrophobicity (*1) | 5.0 |
| 10. | Sericite treated so as to have hydrophobicity (*1) | 2.0 |
| 11. | Talc treated so as to have hydrophobicity (*1) | 3.0 |
| 12. | Iron oxide red treated so as to have hydrophobicity (*1) | 0.4 |
| 13. | Iron oxide yellow treated so as to have hydrophobicity (*1) | 0.7 |
| 14. | Iron oxide black treated so as to have hydrophobicity (*1) | 0.1 |
| 15. | Magnesium sulfate | 0.7 |
| 16. | Glycerin | 3.0 |
| 17. | Antiseptic | proper |
| 18. | Perfume | proper |
| 19. | Purified water | the rest |

(*1) Each powder was rendered hydrophobic by treatment with stearic acid added in a proportion of 2% by weight to the powder.

[Preparation Process]

A: The ingredients 1 to 8 were mixed together under heating, and thereto the ingredients 9 to 14 were added. Then, these mixed ingredients were made homogeneous.

B: The ingredients 15, 16, 17 and 19 were mixed together, and made into a solution by heating.

C: The solution obtained in the step B was added little by little to the homogeneous dispersion obtained in the step A with stirring, thereby making an emulsion. After the emulsion was cooled, the ingredient 18 was added thereto.

The liquid emulsive foundation thus prepared had low viscosity and fine texture, spread smoothly, had neither tacky nor oily feel, and rendered the skin moist, youthful and fresh. Further, it was confirmed that the present foundation ensured durable makeup effect, and besides, caused no change in quality by temperature changes and elapsed time, namely it had very high stability.

EXAMPLE 25

Antiperspirant constituted of the following ingredients was prepared in accordance with the process described below:

| | Ingredients | Amount mixed (wt %) |
|---|---|---|
| 1. | Octamethylcyclopentasiloxane | 30.0 |
| 2. | Silicone compound of Example 9 | 1.0 |
| 3. | Polyoxyethylenesorbitan monooleate (number of oxyethylene units: 20) | 0.5 |
| 4. | Glycine salt of aluminum zirconium tetrachlorohydrate | 20.0 |
| 5. | Purified water | the rest |

[Preparation Process]

A: The ingredients 1 and 2 were mixed together.

B: The ingredient 4 was dissolved in the ingredient 5, and thereto the ingredient 3 was added.

C: The solution obtained in the step B was added little by little to the mixture obtained in the step A with stirring to make an emulsion.

The thus prepared antiperspirant spread smoothly, had neither tacky nor oily feel, little developed a powdery bloom on the applied skin, and gave a refreshing feeling to the users. Further, it was confirmed that the present antiperspirant caused no change in quality by temperature changes and elapsed time, namely it had very high stability.

EXAMPLE 26

Cleansing cream constituted of the following ingredients was prepared in accordance with the process described below:

| | Ingredients | Amount mixed (wt %) |
|---|---|---|
| 1. | Dimethylpolysiloxane (6 cs) | 5.0 |
| 2. | Methylphenylpolysiloxane | 5.0 |
| 3. | Liquid paraffin | 8.0 |
| 4. | Jojoba oil | 2.0 |
| 5. | Silicone compound of Example 1 | 2.5 |
| 6. | Silicone compound of Example 2 | 0.5 |
| 7. | Dextrin fatty acid ester | 0.8 |
| 8. | Aluminum monostearate | 0.2 |
| 9. | Aluminum chloride | 1.0 |
| 10. | Glycerin | 10.0 |
| 11. | Antiseptic | proper |
| 12. | Perfume | proper |
| 13. | Purified water | the rest |

[Preparation Process]

A: The ingredients 1 to 8 were mixed under heating.

B: The ingredients 9, 10, 11 and 13 were mixed and dissolved under heating.

C: The solution obtained in the step B was added little by little to the mixture obtained in the step A with stirring to make an emulsion. After cooling, the emulsion was admixed with the ingredient 12.

The thus prepared cleansing cream had fine texture, spread smoothly, had neither tacky nor oily feel, gave moist and refreshed feelings to the users, and had high cleansing effect. Further, it was confirmed that the present cleansing cream caused no change in quality by temperature changes and elapsed time, namely it had very high stability.

EXAMPLE 27

Cream constituted of the following ingredients was prepared in accordance with the process described below:

| | Ingredients | Amount mixed (wt %) |
|---|---|---|
| 1. | Dimethylpolysiloxane (6 cs) | 7.0 |
| 2. | Methylphenylpolysiloxane | 3.0 |
| 3. | Squalane | 5.0 |
| 4. | Neopentyl glycol dioctanoate | 3.0 |
| 5. | Silicone compound of Example 7 | 3.0 |
| 6. | Aluminum distearate | 0.4 |
| 7. | Magnesium sulfate | 0.7 |
| 8. | Glycerin | 10.0 |
| 9. | Antiseptic | proper |
| 10. | Perfume | proper |
| 11. | Purified water | the rest |

[Preparation Process]
A: The ingredients 1 to 6 were heated, and mixed homogeneously.
B: The ingredients 7, 8, 9 and 11 were mixed and dissolved by heating.
C: The solution obtained in the step B was added little by little to the mixture obtained in the step A with stirring to make an emulsion. After cooling, the emulsion was admixed with the ingredient 10.

The thus prepared cream had fine texture, spread smoothly, had neither tacky nor oily feel, gave moist and fresh feelings to the users, and ensured durable makeup effect. Further, it was confirmed that the present cleansing cream caused no change in quality by temperature changes and elapsed time, namely it had very high stability.

EXAMPLE 28

Cream constituted of the following ingredients was prepared in accordance with the process described below:

| | Ingredients | Amount mixed (wt %) |
|---|---|---|
| 1. | Dimethylpolysiloxane (6 cs) | 6.0 |
| 2. | Methylphenylpolysiloxane | 4.0 |
| 3. | Squalane | 5.0 |
| 4. | Neopentyl glycol dioctanoate | 3.0 |
| 5. | Silicone compound of Example 7 | 3.0 |
| 6. | Fine-grain titanium dioxide treated so as to have hydrophobicity (*1) | 2.0 |
| 7. | Magnesium sulfate | 0.7 |
| 8. | Glycerin | 10.0 |
| 9. | Antiseptic | proper |
| 10. | Perfume | proper |
| 11. | Purified water | the rest |

(*1) The ingredient 6 was prepared as follows: Fine-grain titanium dioxide having an average grain size of 0.05 μm was dispersed into water in a concentration of 10 weight %. Thereto was added a 10 weight % sodium silicate solution ($SiO_2/Na_2O$ ratio: 0.5 by mole) in a proportion of 2 weight % based on the $SiO_2$ to the titanium dioxide. This admixture was stirred thoroughly. Thereafter, a 10 weight % aluminum sulfate solution in an amount corresponding to the proportion of 7.5 weight % based on the $Al_2O_3$ to the titanium dioxide was added gradually to the foregoing admixture, thereby depositing hydrated silicate and hydrated alumina on the grain surface of titanium dioxide. After the conclusion of the reaction, the products were filtered off, washed, dried and then ground with a jet mill. The ground products were transferred into a Henschel mixer, and thereto 2 weight % of methylhydrogenpolysiloxane was added with thorough stirring, followed by baking treatment at 120° C.

[Preparation Process]
A: The ingredients 1 to 5 were mixed together under heating, and therein the ingredient 6 was admixed homogeneously.
B: The ingredients 7, 8, 9 and 11 were mixed together under heating to make a solution.
C: The solution obtained in the step B was added gradually to the mixture obtained in the step A with stirring to make an emulsion. After cooling the emulsion, the ingredient 10 was added to prepare cream.

The thus prepared cream had fine texture, spread smoothly, had neither tacky nor oily feel, and gave moist, youthful and refreshed feelings to the users. Further, it was confirmed that the present cream ensured durable makeup effect, and besides, caused no change in quality by temperature changes and elapsed time, namely it had very high stability.

EXAMPLE 29

Transparent cosmetic jell constituted of the following ingredients was prepared in accordance with the process described below:

| | Ingredients | Amount mixed (wt %) |
|---|---|---|
| 1. | Decamethylcyclopentasiloxane | 10.0 |
| 2. | Silicone compound of Example 9 | 10.0 |
| 3. | 1,3-Butylene glycol | 10.0 |
| 4. | Polyethylene glycol 400 | 9.0 |
| 5. | 2-Hydroxyoctanoic acid | 1.0 |
| 6. | Sorbitol (70% aq. soln.) | 10.0 |
| 7. | Citric acid | proper |
| 8. | Sodium citrate | proper |
| 9. | Antiseptic | proper |
| 10. | Perfume | proper |
| 11. | Purified water | the rest |

[Preparation Process]
A: The ingredients 3 to 11 were mixed and made into a homogenous solution.
B: The ingredients 1 and 2 were mixed homogeneously.
C: The solution obtained in the step A was added little by little to the mixture obtained in the step B with stirring, thereby making an emulsion.

The thus prepared transparent cosmetic jell spread smoothly, had neither tacky nor oily feel, and gave moist and fresh feelings to the users. In addition, the skin absorbed this cosmetic jell well. Further, it was confirmed that the cosmetic jell caused no change in quality by temperature changes and elapsed time, namely it had very high stability.

EXAMPLE 30

Sunscreen lotion constituted of the following ingredients was prepared in accordance with the process described below:

| | Ingredients | Amount mixed (wt %) |
|---|---|---|
| 1. | Decamethylcylopentasiloxane | 14.0 |
| 2. | Silicone compound of Example 9 | 10.0 |
| 3. | Squalane | 1.5 |
| 4. | Octyl paramethoxycinnamate | 3.0 |
| 5. | Superfine-grain titanium dioxide treated so as to have hydrophobicity (*1) | 2.0 |
| 6. | 1.3-Butylene glycol | 10.0 |
| 7. | Sodium chloride | 2.0 |
| 8. | L-Proline | 0.1 |
| 9. | 2-Hydroxyoctanoic acid | 1.0 |

-continued

| | Ingredients | Amount mixed (wt %) |
|---|---|---|
| 10. | 2-Hyddroxypropanoic acid | 5.0 |
| 11. | Sodium Hydroxide | proper |
| 12. | Antiseptic | proper |
| 13. | Perfume | proper |
| 14. | Purified water | the rest |

(*1) Titan TTO-S2 (trade name, a product of ISHIHARA SANGYO KAISHA Ltd.)

[Preparation Process]

A: The ingredients 6 to 14 were mixed and made into a homogeneous solution.

B: The ingredients 1 to 4 were mixed, and thereto the ingredient 5 was added. The resulting mixture was made homogenous.

C: The mixture obtained in the step B was added little by little to the solution obtained in the step A with stirring, thereby making an emulsion.

The thus prepared sunscreen lotion spread smoothly, had neither tacky nor oily feel, and gave moist and fresh feelings to the users. Moreover, this lotion was absorbed well by the skin and had high sunscreen effect. In addition, it was confirmed that this lotion caused no change in quality by temperature changes and elapsed time, namely it had very high stability.

EXAMPLE 31

Cream constituted of the following ingredients was prepared in accordance with the process described below:

| | Ingredients | Amount mixed (wt %) |
|---|---|---|
| 1. | Decamethylcyclopentasiloxane | 20.0 |
| 2. | Liquid paraffin | 5.0 |
| 3. | Silicone compound of Example 7 | 1.0 |
| 4. | Magnesium salt of L-ascorbic acid phosphoric ester | 3.0 |
| 5. | Dipropylene glycol | 5.0 |
| 6. | Glycerin | 5.0 |
| 7. | Antiseptic | proper |
| 8. | Perfume | proper |
| 9. | Purified water | the rest |

[Preparation Process]

A: The ingredients 1 to 3 were mixed homogeneously.

B: The ingredients 5 to 7 were warmed and mixed homogeneously.

C: The ingredient 4 and 9 were mixed and made into a homogeneous solution.

D: To the mixture obtained in the step A with stirring, the solution obtained in the step B was added little by little, and further the solution obtained in the step C was added to make an emulsion. Then, the emulsion was admixed with the ingredient 8.

The thus prepared cream had fine texture, spread smoothly, had neither tacky nor oily feel, and rendered the users' skin moist, youthful and fresh. In addition, this cream was absorbed well by the skin and had excellent whitening effect. Further, it was confirmed that the cream caused no change in quality by temperature changes and elapsed time, namely it had very high stability.

EXAMPLE 32

Milky lotion constituted of the following ingredients was prepared in accordance with the process described below:

| | Ingredients | Amount mixed (wt %) |
|---|---|---|
| 1. | Decamethylcyclopentasiloxane | 18.0 |
| 2. | Dimethylpolysiloxane (6 cs) | 6.0 |
| 3. | Squalane | 5.0 |
| 4. | Neopentyl glycol dioctanoate | 3.0 |
| 5. | α-Monooleyl glyceryl ether | 1.0 |
| 6. | Silicone compound of Example 3 | 2.0 |
| 7. | Aluminum distearate | 0.2 |
| 8. | Magnesium sulfate | 0.7 |
| 9. | Glycerin | 5.0 |
| 10. | Antiseptic | proper |
| 11. | Perfume | proper |
| 12. | Purified water | the rest |

[Preparation Process]

A: The ingredients 1 to 7 were mixed together under heating.

B: The ingredients 8, 9, 10 and 12 were mixed together, and made into a solution by heating.

C: The solution obtained in the step B was added little by little to the mixture obtained in the step A with stirring, thereby making an emulsion. After the emulsion was cooled, the ingredient 11 was added thereto.

The milky lotion thus prepared had low viscosity and fine texture, spread smoothly, had neither tacky nor oily feel, and gave moist, youthful and refreshed feelings to the users. Further, it was confirmed that this milky lotion ensured durable makeup effect, and besides, caused no change in quality by temperature changes and elapsed time, namely it had very high stability.

EXAMPLE 33

Milky lotion constituted of the following ingredients was prepared in accordance with the process described below:

| | Ingredients | Amount mixed (wt %) |
|---|---|---|
| 1. | Decamethylcyclopentasiloxane | 15.0 |
| 2. | Dimethylpolysiloxane (6 cs) | 6.0 |
| 3. | Squalane | 5.0 |
| 4. | Neopentyl glycol dioctanoate | 3.0 |
| 5. | α-Monooleyl glyceryl ether | 1.0 |
| 6. | Organopolysiloxane modified by both polyoxyalkylene and alkyl groups (*1) | 1.5 |
| 7. | Silicone compound of Example 4 | 1.0 |
| 8. | Aluminum distearate | 0.2 |
| 9. | Dextrin fatty acid ester | 1.0 |
| 10. | Magnesium sulfate | 0.7 |
| 11. | Glycerin | 5.0 |
| 12. | Antiseptic | proper |
| 13. | Perfume | proper |
| 14. | Purified water | the rest |

(*1) KF6026 (trade name, a product of SHIN-ETSU CHEMICAL Co., Ltd.)

[Preparation Process]

A: The ingredients 1 to 9 were mixed together under heating.

B: The ingredients 10, 11, 12 and 14 were mixed together, and made into a solution by heating.

C: The solution obtained in the step B was added little by little to the mixture obtained in the step A with stirring, thereby making an emulsion. After the emulsion was cooled, the ingredient 13 was added thereto.

The milky lotion thus prepared had low viscosity and fine texture, spread smoothly, had neither tacky nor oily feel, and gave moist, youthful and refreshed feelings to the users. Further, it was confirmed that this milky lotion ensured durable makeup effect, and besides, caused no change in quality by temperature changes and elapsed time, namely it had very high stability.

EXAMPLE 34

Sunscreen cream constituted of the following ingredients was prepared in accordance with the process described below:

|  | Ingredients | Amount mixed (wt %) |
|---|---|---|
| 1. | Decamethylcylopentasiloxane | 18.0 |
| 2. | Methylphenylpolysiloxane | 2.0 |
| 3. | Liquid paraffin | 1.5 |
| 4. | Silicone compound of Example 3 | 4.0 |
| 5. | Octyl paramethoxycinnamate | 5.0 |
| 6. | 1.3-Butylene glycol | 4.0 |
| 7. | Sodium chloride | 1.0 |
| 8. | Antiseptic | proper |
| 9. | Perfume | proper |
| 10. | Purified water | the rest |

[Preparation Process]
A: The ingredients 1 to 5 were mixed under heating.
B: The ingredients 6, 7, 8 and 10 were mixed and dissolved under heating.
C: The solution obtained in the step B was added little by little to the mixture obtained in the step A with stirring, thereby making an emulsion. After cooling, the emulsion was admixed with the ingredient 9.

The thus prepared sunscreen cream had fine texture, spread smoothly, and had excellent usability because it had neither tacky nor oily feel but gave moist and fresh feelings to the users. Moreover, this cream ensured durable makeup effect because of its high resistance to water and perspiration, and kept its UV protection effect for a long time. In addition, it was confirmed that this cream caused no change in quality by temperature changes and elapsed time, namely it had very high stability.

EXAMPLE 35

Cream constituted of the following ingredients was prepared in accordance with the process described below:

|  | Ingredients | Amount mixed (wt %) |
|---|---|---|
| 1. | Decamethylcylopentasiloxane | 20.0 |
| 2. | Methylphenylpolysiloxane | 5.0 |
| 3. | Silicone compound of Example 3 | 1.0 |
| 4. | Dextrin fatty acid ester | 1.0 |
| 5. | Glycerin | 5.0 |
| 6. | Sodium chloride | 1.0 |
| 7. | Antiseptic | proper |
| 8. | Perfume | proper |
| 9. | Purified water | the rest |

[Preparation Process]
A: The ingredients 1 to 4 were mixed under heating.
B: The ingredients 5, 6, 7 and 9 were mixed and dissolved under heating.
C: The solution obtained in the step B was added little by little to the mixture obtained in the step A with stirring, thereby making an emulsion. After cooling, the emulsion was admixed with the ingredient 8.

The thus prepared cream had fine texture, spread smoothly, and had excellent usability because it had neither tacky nor oily feel but gave moist and fresh feelings to the users. Moreover, this cream ensured durable makeup effect because of its high resistance to water and perspiration, and the duration of its UV protection effect was long. In addition, it was confirmed that this cream caused no change in quality by temperature changes and elapsed time, namely it had very high stability.

EXAMPLE 36

Foundation constituted of the following ingredients was prepared in accordance with the process described below:

|  | Ingredients | Amount mixed (wt %) |
|---|---|---|
| 1. | Decamethylcylopentasiloxane | 18.0 |
| 2. | Methylphenylpolysiloxane | 5.0 |
| 3. | Sorbitan monoisostearate | 0.5 |
| 4. | Diglyceryl monoisostearate | 0.5 |
| 5. | Silicone compound of Example 9 | 1.0 |
| 6. | Octyl paramethoxycinnamate | 3.0 |
| 7. | Titanium dioxide | 10.0 |
| 8. | Iron oxide red | 0.13 |
| 9. | Iron oxide yellow | 0.3 |
| 10. | Iron oxide black | 0.07 |
| 11. | Talc | 2.5 |
| 12. | Sorbitol | 2.0 |
| 13. | Magnesium sulfate | 0.1 |
| 14. | Ethanol | 10.0 |
| 15. | Antiseptic | proper |
| 16. | Perfume | proper |
| 17. | Purified water | the rest |

[Preparation Process]
A: The ingredients 7 to 11 were mixed homogeneously.
B: The ingredients 1 to 6 and 15 were mixed under heating, and then added to the mixture obtained in the step A to make a homogeneous dispersion.
C: The ingredients 12, 13 and 17 were warmed and mixed, and then added to the dispersion obtained in the step B, thereby making an emulsion. After cooling, the emulsion was admixed with the ingredients 14 and 16.

The thus prepared foundation had no tackiness, spread smoothly, and gave a strong feeling of refreshment to the users. And it was in a good emulsified condition. Further, it was confirmed that this foundation was little affected by temperature changes, and caused neither separation nor condensation, namely it had very high stability.

EXAMPLE 37

Liquid foundation constituted of the following ingredients was prepared in accordance with the process described below:

|  | Ingredients | Amount mixed (wt %) |
|---|---|---|
| 1. | Decamethylcylopentasiloxane | 15.0 |
| 2. | Dimethylpolysiloxane (6 cs) | 5.0 |
| 3. | Liquid Paraffin | 3.0 |
| 4. | Silicon compound of Example 1 | 1.5 |
| 5. | Polyoxyalkylene-modified silicone (*1) | 1.5 |

-continued

| | Ingredients | Amount mixed (wt %) |
|---|---|---|
| 6. | Palmitic acid | 0.5 |
| 7. | Hydrophobic silica (*2) | 5.0 |
| 8. | Titanium dioxide | 6.0 |
| 9. | Iron oxide red | 0.25 |
| 10. | Iron oxide yellow | 0.6 |
| 11. | Iron oxide black | 0.12 |
| 12. | Sericite | 8.03 |
| 13. | Dipropylene glycol | 10.0 |
| 14. | Magnesium sulfate | 2.0 |
| 15. | Antiseptic | proper |
| 16. | Antioxidant | proper |
| 17. | Perfume | proper |
| 18. | Purified water | the rest |

(*1) KF-6017 (trade name, produced by SHIN-ETSU CHEMICAL Co., Ltd.)
(*2) Aerosil RY200 (trade name, produced by Nippon Aerosil Co., Ltd.)

[Preparation Process]
A: The ingredients 8 to 12 were mixed homogeneously.
B: The ingredients 1 to 7 and 16 were mixed while heating at 70° C., and then added to the mixture obtained in the step A to make a homogeneous dispersion.
C: The ingredients 13 to 18 were heated at 70° C., and then added to the dispersion obtained in the step B, thereby making an emulsion. After cooling, the emulsion was admixed with the ingredients 17.

The thus prepared liquid foundation had no tackiness, spread smoothly, and gave a strong feeling of refreshment to the users. And it was in a good emulsified condition and had durable makeup effect. Further, it was confirmed that this foundation was little affected by temperature changes, and had very high stability.

EXAMPLE 38

Sunscreen milk constituted of the following ingredients was prepared in accordance with the process described below:

| | Ingredients | Amount mixed (wt %) |
|---|---|---|
| 1. | Decamethylcylopentasiloxane | 25.0 |
| 2. | Diglyceryl monoisostearate | 1.5 |
| 3. | Decaglyceryl pentaisostearate | 1.5 |
| 4. | Silicone compound of Example 5 | 0.5 |
| 5. | Olive oil | 1.0 |
| 6. | Fine-grain titanium dioxide | 7.0 |
| 7. | Glycerin | 5.0 |
| 8. | Sodium chloride | 1.5 |
| 9. | Antiseptic | proper |
| 10. | Perfume | proper |
| 11. | Purified water | the rest |

[Preparation Process]
A: The ingredients 1 to 5 were mixed together under heating, and therein the ingredient 6 was dispersed homogeneously.
B: The ingredients 7, 8 and 11 were mixed under heating.
C: The mixture obtained in the step B was added little by little to the dispersion obtained in the step A with stirring, thereby making an emulsion. After the emulsion was cooled, the ingredient 10 was added thereto.

The sunscreen milk thus prepared had a low viscosity and fine texture, spread smoothly, and had no tackiness. And it gave a moist and fresh feel to the milk-applied skin. In addition, it ensured durable makeup effect, and kept its UV protection effect for a long time. Further, it was confirmed that this sunscreen milk was little affected by storage temperature and time, and the powder-dispersed state and emulsified state thereof was kept stable for a long time.

EXAMPLE 39

Sunscreen milk constituted of the following ingredients was prepared in accordance with the process described below:

| | Ingredients | Amount mixed (wt %) |
|---|---|---|
| 1. | Decamethylcylopentasiloxane | 20.0 |
| 2. | Methylphenylpolysiloxane | 3.0 |
| 3. | Sorbitan monoisostearate | 1.0 |
| 4. | Silicone compound of Example 9 | 0.5 |
| 5. | Trimethylsiloxysilicic acid | 1.0 |
| 6. | Octyl paramethoxycinnamate | 4.0 |
| 7. | Fine-grain titanium dioxide | 8.0 |
| 8. | Sorbitol | 2.0 |
| 9. | Sodium chloride | 2.0 |
| 10. | Antiseptic | proper |
| 11. | Perfume | proper |
| 12. | Purified water | the rest |

[Preparation Process]
A: The ingredients 1 to 6 were mixed together under heating, and therein the ingredient 7 was dispersed homogeneously.
B: The ingredients 8 to 10 and 12 were mixed under heating.
C: The mixture obtained in the step B was added little by little to the dispersion obtained in the step A with stirring, thereby making an emulsion. After the emulsion was cooled, the ingredient 11 was added thereto.

The sunscreen milk thus prepared had fine texture, spread smoothly, and had no tackiness. And it gave a moist and fresh feel to the milk-applied skin. In addition, it ensured durable makeup effect, and kept its UV protection effect for a long time. Further, it was confirmed that this sunscreen milk caused no change in quality by temperature changes and elapsed time, namely it had very high stability.

EXAMPLE 40

Beauty-care lotion (or moisturing essence) constituted of the following ingredients was prepared in accordance with the process described below:

| | Ingredients | Amount mixed (wt %) |
|---|---|---|
| 1. | Decamethylcylopentasiloxane | 12.0 |
| 2. | Glyceryl triisooctanoate | 10.0 |
| 3. | Organopolysiloxane modified by both polyoxyalkylene and alkyl groups (*1) | 2.0 |
| 4. | Silicone compound of Example 4 | 0.2 |
| 5. | Glycerin | 10.0 |
| 6. | Magnesium salt of ascorbic acid phosphoric ester | 3.0 |
| 7. | Sodium chloride | 2.0 |
| 8. | Antiseptic | proper |
| 9. | Perfume | proper |
| 10. | Purified water | the rest |

(*1) KE6026 (trade name, a product of SHIN-ETSU CHEMICAL Co., Ltd.)

[Preparation Process]
A: The ingredients 1 to 4 were mixed together under heating.
B: The ingredients 5 to 8 and 10 were heated and dissolved homogeneously.
C: The solution obtained in the step B was added little by little to the mixture obtained in the step A with stirring, thereby making an emulsion. After the emulsion was cooled, the ingredient 9 was added thereto.

The beauty-care lotion thus prepared had fine texture, spread smoothly, and had no tackiness. And it gave moist and youthful feelings to the users. Further, it was confirmed that this lotion caused no change in quality by temperature changes and elapsed time.

EXAMPLE 41

Cream constituted of the following ingredients was prepared in accordance with the process described below:

|  | Ingredients | Amount mixed (wt %) |
| --- | --- | --- |
| 1. | Decamethylcylopentasiloxane | 18.0 |
| 2. | Dimethylpolysiloxane (100 cs) | 2.0 |
| 3. | Polypropylene glycol (3) myristyl ether | 0.5 |
| 4. | Silicone compound of Example 6 | 2.5 |
| 5. | Fine-grain titanium dioxide treated so as to have hydrophobicity (*1) | 1.0 |
| 6. | Glycerin | 3.0 |
| 7. | Sorbitol (70% aq. soln.) | 5.0 |
| 8. | Citric acid | 25.0 |
| 9. | Sodium chloride | 0.6 |
| 10. | Antiseptic | proper |
| 11. | Perfume | proper |
| 12. | 32% aqueous ammonia | 4.5 |
| 13. | Purified water | the rest |

(*1) Fine-grain titanium dioxide treated with aluminum stearate.

[Preparation Process]
A: The ingredients 1 to 4 and 11 were mixed together, and further admixed with the ingredient 5 with stirring.
B: The ingredients 6 to 10, 12 and 13 were dissolved homogeneously.
C: The solution obtained in the step B was added little by little to the mixture obtained in the step A, thereby making an emulsion.

The thus prepared cream spread smoothly although it contained a large amount of citric acid, and had no tackiness. In addition, the cream-applied skin felt moist and smooth. Further, it was confirmed that the cream caused no change in quality by temperature changes and elapsed time, namely it had very high stability.

EXAMPLE 42

Wash-away type facial pack constituted of the following ingredients was prepared in accordance with the process described below:

|  | Ingredients | Amount mixed (wt %) |
| --- | --- | --- |
| 1. | Dimethylpolysiloxane (6 cs) | 3.0 |
| 2. | Silicone compound of Example 2 | 2.0 |
| 3. | Kaolin | 30.0 |
| 4. | Carboxyvinyl polymer | 0.4 |
| 5. | 1,3-Butylene glycol | 10.0 |
| 6. | Glycerin | 20.0 |
| 7. | Antiseptic | proper |

-continued

|  | Ingredients | Amount mixed (wt %) |
| --- | --- | --- |
| 8. | Perfume | proper |
| 9. | Purified water | the rest |

[Preparation Process]
A: The ingredients 1, 2 and 8 were mixed together.
B: The ingredients 4 to 7 and 9 were mixed homogeneously, and further admixed with the ingredient 3 with stirring.
C: The mixture obtained in the step A was added to the mixture obtained in the step B to make an emulsion. Thus, a wash-away type facial pack in a paste state was prepared.

The thus prepared facial pack spread smoothly, and had excellent cleansing effect. In addition, it gave pleasant feelings to the users. Specifically, after the facial pack was washed away, the face had moist, soft and smooth feel but no tackiness. Further, it was confirmed that the facial pack had excellent stability.

EXAMPLE 43

Wipe-off type cleansing cream constituted of the following ingredients was prepared in accordance with the process described below:

|  | Ingredients | Amount mixed (wt %) |
| --- | --- | --- |
| 1. | Squalane | 10.0 |
| 2. | Liquid paraffin | 28.0 |
| 3. | Low-density polyethylene | 2.0 |
| 4. | Silicone compound of Example 9 | 2.0 |
| 5. | Propylene glycol | 5.0 |
| 6. | Antioxidant | proper |
| 7. | Antiseptic | proper |
| 8. | Perfume | proper |
| 9. | Purified water | the rest |

[Preparation Process]
A: The ingredients 1 to 4 and 6 to 8 were mixed under heating.
B: The ingredients 5 and 9 were mixed under heating, and then added to the mixture obtained in the step A with stirring to make an emulsion.

The thus prepared wipe-off type cleansing cream spread smoothly, and had no tackiness. After it was wiped off, the face had moist and dry feel. Further, it was confirmed that the cleansing cream caused no change in quality by temperature changes and elapsed time, namely it had very high stability.

EXAMPLE 44

After-shave cream constituted of the following ingredients was prepared in accordance with the process described below:

|  | Ingredients | Amount mixed (wt %) |
| --- | --- | --- |
| 1. | Decamethylcylopentansiloxane | 35.0 |
| 2. | Silicone compound of Example 9 | 5.0 |

-continued

| | Ingredients | Amount mixed (wt %) |
|---|---|---|
| 3. | Polyethylene glycol (molecular weight: 400) | 5.0 |
| 4. | Sodium L-glutamate | 2.0 |
| 5. | Allantoin | 0.1 |
| 6. | Aloe extract | proper |
| 7. | Antiseptic | proper |
| 8. | Antioxidant | proper |
| 9. | Perfume | proper |
| 10. | Purified water | the rest |

[Preparation Process]

A: The ingredients 1 to 3, 9 and 10 were mixed under heating.
B: The ingredients 4 to 8 were mixed under heating.
C: The mixture obtained in the step B was added to the mixture obtained in the step A to make an emulsion.

When applied to the face, the thus prepared after-shave cream didn't trickle down the face because of its high viscosity, but spread smoothly and had no tackiness. The cream applied to the face had moist and smooth feel, and gave a pleasant feeling to the users. Further, it was confirmed that this after-shave cream had high stability.

EXAMPLE 45

Deodorant constituted of the following ingredients was prepared in accordance with the process described below:

| | Ingredients | Amount mixed (wt %) |
|---|---|---|
| 1. | Decamethylcylopentansiloxane | 12.0 |
| 2. | Dimethylpolysiloxane (6 cs) | 4.0 |
| 3. | Silicone compound of Example 2 | 1.0 |
| 4. | Propylene glycol | 31.0 |
| 5. | Triclosan | 0.1 |
| 6. | Glycerin | 15.0 |
| 7. | Antiseptic | proper |
| 8. | Perfume | proper |
| 9. | Purified water | the rest |

[Preparation Process]

A: The ingredients 1 to 3 were mixed.
B: The ingredient 5 was dissolved in the ingredient 4, and further admixed with the ingredients 6 to 9.
C: The mixture obtained in the step A was stirred vigorously, and thereto the mixture obtained in the step B was added to make an emulsion.
D: The emulsion obtained in the step C in an amount of 65 parts by weight and a jetting agent (mixture of n-butane, isobutane and propane) in an amount of 35 parts by weight were charged into aerosol cans.

The thus prepared deodorant had excellent usability, because it didn't trickled down even when used in a high concentration, but it had a dry and smooth feel. Further, the duration of its effect was long.

EXAMPLE 46

Liquid foundation constituted of the following ingredients was prepared in accordance with the process described below:

| | Ingredients | Amount mixed (wt %) |
|---|---|---|
| 1. | Decamethylcylopentansiloxane | 16.0 |
| 2. | Dimethylpolysiloxane (6 cs) | 8.0 |
| 3. | Octyl paramethoxycinnamate | 3.0 |
| 4. | 12-Hydroxystearic acid | 1.0 |
| 5. | Fluorine-modified silicone (*1) | 15.0 |
| 6. | Silicone compound of Example 10 | 5.0 |
| 7. | Spherical silicone resin powder (*2) | 3.0 |
| 8. | Fluorine compound-treated fine-grain titanium dioxide (*3) | 8.0 |
| 9. | Fluorine compound-treated titanium mica (*3) | 1.0 |
| 10. | Fluorine compound-treated titanium dioxide (*3) | 5.0 |
| 11. | Fluorine compound-treated iron oxide red (*3) | 0.9 |
| 12. | Fluorine compound-treated iron oxide yellow (*3) | 2.0 |
| 13. | Fluorine compound-treated iron oxide black (*3) | 1.0 |
| 14. | Ethanol | 15.0 |
| 15. | Glycerin | 3.0 |
| 16. | Magnesium sulfate | 1.0 |
| 17. | Antiseptic | proper |
| 18. | Perfume | proper |
| 19. | Purified water | the rest |

(*1) FL-100 (trade name, produced by SHIN-ETSU CHEMICAL Co., Ltd.)
(*2) KMP590 (trade name, produced by SHIN-ETSU CHEMICAL Co., Ltd.)
(*3) Each powder was treated with diethanolamine salt of perfluoroalkyl-ethylphosphoric acid added in a proportion of 5% to the powder.

[Preparation Process]
A: The ingredients 7 to 13 were mixed homogeneously.
B: The ingredients 1 to 6 were mixed while heating at 70° C., and thereto the mixture obtained in the step A was added to make a homogeneous dispersion.
C: The ingredients 14 to 17 and 19 were warmed to 40° C., and then added to the dispersion obtained in the step B, thereby making an emulsion. After cooling, the emulsion was admixed with the ingredients 18.

The thus prepared liquid foundation had no tackiness, spread smoothly, and gave a strong feeling of refreshment to the users. Further, it was confirmed that this foundation caused no change in quality by temperature changes and elapsed time, namely it had very high stability.

EXAMPLE 47

Sunscreen milk constituted of the following ingredients was prepared in accordance with the process described below:

| | Ingredients | Amount mixed (wt %) |
|---|---|---|
| 1. | Pentaerythritol tetra-2-ethylhexanoate | 10.0 |
| 2. | Cetyl 2-ethylhexanoate | 5.0 |
| 3. | Squalane | 10.0 |
| 4. | Silicone compound of Example 1 | 3.0 |
| 5. | Octyl paramethoxycinnamate | 2.0 |
| 6. | 2,4-Dihydroxybenzophenone | 5.0 |
| 7. | Spherical composite powder of organo- | 1.5 |

-continued

| | Ingredients | Amount mixed (wt %) |
|---|---|---|
| | polysiloxane elastomer (*1) | |
| 8. | Hydrophobic silica (*2) | 0.5 |
| 9. | Polyethylene glycol 6000 | 1.0 |
| 10. | Propylene glycol | 8.0 |
| 11. | Antiseptic | proper |
| 12. | Perfume | proper |
| 13. | Purified water | the rest |

(*1) KSP-1 (trade name, produced by SHIN-ETSU CHEMICAL Co., Ltd.)
(*2) Aerosil R972 (trade name, produced by Nippon Aerosil Co., Ltd.)

[Preparation Process]
A: The ingredients 5 and 6 were dissolved homogeneously in a part of the ingredient 1.
B: The ingredients 2 to 4 were mixed with the rest of the ingredient 1, and thereto the solution obtained in the step A was added. Therein, the ingredients 7 and 8 were mixed and dispersed homogeneously.
C: The ingredient 9 was added to the ingredient 13, and dissolved therein, and thereto homogeneously mixed ingredients 10 and 11 were added.
D: The admixture obtained in the step C was added little by little to the dispersion obtained in the step B to make an emulsion. The emulsion prepared was cooled, and thereto the ingredient 12 was added.

The thus prepared sunscreen milk spread easily, and had dry and smooth feel. Further, it was confirmed that this milk had excellent usability and stability, and caused no change in quality by temperature changes and elapsed time.

EXAMPLE 48

Milky lotion constituted of the following ingredients was prepared in accordance with the process described below:

| | Ingredients | Amount mixed (wt %) |
|---|---|---|
| 1. | Decamethylcyclopentasiloxane | 15.0 |
| 2. | Methylphenylpolysiloxane | 5.0 |
| 3. | Squalane | 5.0 |
| 4. | Pentaerythritol tetra-2-ethylhexanoate | 5.0 |
| 5. | Silicone compound of Example 1 | 3.0 |
| 6. | Spherical powder of organopolysiloxane elastomer (*1) | 2.0 |
| 7. | Hydrophobic silica (*2) | 0.5 |
| 8. | Magnesium salt of ascorbic acid phosphoric ester | 1.0 |
| 9. | Sodium chloride | 1.0 |
| 10. | Polyethylene glycol 11000 | 1.0 |
| 11. | Propylene glycol | 8.0 |
| 12. | Antiseptic | proper |
| 13. | Perfume | proper |
| 14. | Purified water | the rest |

(*1) KMP594 (trade name, produced by SHIN-ETSU CHEMICAL Co., Ltd.)
(*2) Aerosil R972 (trade name, produced by Nippon Aerosil Co., Ltd.)

[Preparation Process]
A: The ingredients 1 to 5 were mixed homogeneously, and thereto the ingredients 6 and 7 were added and made into a homogeneous dispersion.
B: The ingredients 8 to 10 were added to the ingredient 14, and dissolved therein, and thereto homogeneously mixed ingredients 11 and 12 were added.
C: The admixture obtained in the step B was added little by little to the dispersion obtained in the step A to make an emulsion. The emulsion prepared was cooled, and thereto the ingredient 13 was added.

The thus prepared milky lotion spread easily, and had dry and smooth feel. Further, it was confirmed that this lotion had excellent usability and stability, and caused no change in quality by temperature changes and elapsed time.

EXAMPLE 49

Moisture-retentive cream constituted of the following ingredients was prepared in accordance with the process described below:

| | Ingredients | Amount mixed (wt %) |
|---|---|---|
| 1. | Decamethylcylopentasiloxane | 10.0 |
| 2. | Methylphenylpolysiloxane | 3.0 |
| 3. | Liquid paraffin | 5.0 |
| 4. | Pentaerythritol tetra-2-ethylhexanoate | 3.0 |
| 5. | Cetyl 2-ethylhexanoate | 5.0 |
| 6. | Silicone compound of Example 1 | 1.0 |
| 7. | Spherical powder of organopolysiloxane elastomer (*1) | 2.5 |
| 8. | Hydrophobic silica (*2) | 2.0 |
| 9. | Zinc stearate | 2.0 |
| 10. | Vitamin E acetate | 3.0 |
| 11. | Polyethylene glycol 400 | 1.0 |
| 12. | Sodium lactate | 1.0 |
| 13. | 1,3-Butylene glycol | 5.0 |
| 14. | Antiseptic | proper |
| 15. | Perfume | proper |
| 16. | Purified water | the rest |

(*1) KMP594 (trade name, produced by SHIN-ETSU CHEMICAL Co., Ltd.)
(*2) Aerosil R972 (trade name, produced by Nippon Aerosil Co., Ltd.)

[Preparation Process]
A: The ingredients 1 to 6, 9 and 10 were mixed homogeneously, and thereto the ingredients 7 and 8 were added and made into a homogeneous dispersion.
B: The ingredients 11 to 14 and 16 were added, and made into a solution.
C: The solution obtained in the step B was added little by little to the dispersion obtained in the step A to make an emulsion. The emulsion prepared was cooled, and thereto the ingredient 15 was added.

The thus prepared moisture-retentive cream spread easily, and had moist, fresh and smooth feel. Further, it was confirmed that this cream had excellent usability and stability, and caused no change in quality by temperature changes and elapsed time.

EXAMPLE 50

Hand cream constituted of the following ingredients was prepared in accordance with the process described below:

| | Ingredients | Amount mixed (wt %) |
|---|---|---|
| 1. | Decamethylcyclopentasiloxane | 30.0 |
| 2. | Liquid paraffin | 10.0 |
| 3. | Amino-modified silicone rubber (*1) | 15.0 |
| 4. | Silicone compound of Example 1 | 4.0 |
| 5. | Distearyldimethylammonium chloride | 0.8 |
| 6. | Vitamin E acetate | 0.1 |
| 7. | Polyethylene glycol 4000 | 1.0 |
| 8. | Glycerin | 10.0 |
| 9. | Aluminum magnesium silicate | 1.2 |

-continued

| | Ingredients | Amount mixed (wt %) |
|---|---|---|
| 10. | Antiseptic | proper |
| 11. | Perfume | proper |
| 12. | Purified water | the rest |

(*1) Amine equivalent: 70,000 g/mole

[Preparation Process]

A: The ingredients 1 and 3 were mixed and dissolved under heating, and thereto the ingredients 2, 4 to 6 and 10 were added under heating.
B: The ingredients 7 to 9 and 12 were mixed under heating.
C: The mixture obtained in the step B was added little by little to the solution obtained in the step A, thereby making an emulsion. After the emulsion was cooled, the ingredient 11 was added thereto.

The thus prepared hand cream had no tackiness, spread easily, and the cream-applied hand had a dry feel. Further, it was confirmed that this cream protected effectively hands from washing-work damage and had very high temperature stability.

EXAMPLE 51

Eyeliner constituted of the following ingredients was prepared in accordance with the process described below:

| | Ingredients | Amount mixed (wt %) |
|---|---|---|
| 1. | Decamethylcylopentanesiloxane | 22.0 |
| 2. | Dimethylpolysiloxane (6 cs) | 5.0 |
| 3. | Silicone-treated iron oxide black | 20.0 |
| 4. | Vitamin E acetate | 0.2 |
| 5. | Jojoba oil | 2.0 |
| 6. | Bentonite | 3.0 |
| 7. | Silicone compound of Example 10 | 2.0 |
| 8. | Ethanol | 10.0 |
| 9. | 1,3-Butylene glycol | 10.0 |
| 10. | Antiseptic | proper |
| 11. | Perfume | proper |
| 12. | Purified water | the rest |

[Preparation Process]

A: The ingredients 1 and 2 were mixed with the ingredients 4 to 7, and therein the ingredient 3 was further mixed and dispersed homogeneously.
B: The ingredients 8, 9, 10 and 12 were mixed together.
C: The mixture obtained in the step B was added little by little to the dispersion obtained in the step A to make an emulsion. After cooling the emulsion, the ingredient 11 was added thereto.

The thus prepared eyeliner spread smoothly, and so the users thereof were able to outline the eyes easily. Further, this eyeliner had no tacky feel, but provided cool and dry feelings to the users. In addition, it was confirmed that the present eyeliner caused no change in quality by temperature changes and lapsed time, it had very excellent usability and stability, and the duration of its effect was very long because of its high resistance to water and sweat.

EXAMPLE 52

Cream constituted of the following ingredients was prepared in accordance with the process described below:

| | Ingredients | Amount mixed (wt %) |
|---|---|---|
| 1. | Decamethylcyclopentasiloxane | 16.0 |
| 2. | Dimethylpolysiloxane (6 cs) | 4.0 |
| 3. | Silicone compound of Example 9 | 5.0 |
| 4. | Polyoxyethylene (5) octyl dodecyl ether | 1.0 |
| 5. | Polyoxyethylene (20) sorbitan monostearic acid ester | 0.5 |
| 6. | Zinc oxide treated with silica (*1) | 2.0 |
| 7. | Silicone-treated fine-grained titanium dioxide | 10.0 |
| 8. | Liquid paraffin | 2.0 |
| 9. | Macadamia nut oil | 1.0 |
| 10. | Scutellariae radix extract (*2) | 1.0 |
| 11. | Gentian root extract (*3) | 0.5 |
| 12. | Ethanol | 5.0 |
| 13. | 1,3-Butylene glycol | 2.0 |
| 14. | Antiseptic | proper |
| 15. | Perfume | proper |
| 16. | Purified water | the rest |

(*1) Silica having grain sizes of from 0.01 to 10 μm wherein zinc oxide is encapsulated in a proportion of 50%; SUNSPHERE SZ-5 (trade name, a product of ASAHI GLASS CO., LTD.)
(*2) Essence extracted with 50% 1,3-butylene glycol water
(*3) Essence extracted with 20% ethanol water

[Preparation Process]

A: The ingredients 6 to 9 were mixed to make a dispersion.
B: The ingredients 1 to 5 were mixed, and thereto the dispersion obtained in the step A was added.
C: The ingredients 10 to 14 were mixed with the ingredient 16, and thereto the mixture obtained in the step B was added to make an emulsion.
D: After the emulsion was cooled, the ingredient 15 was added thereto.

The thus prepared cream had no tacky feel, not only spread smoothly but also provided a clingy feeling and fitted in with the skin, and further ensured lustrous finish and durable makeup effects. In addition, it was confirmed that the present cream caused no change in quality by temperature changes and lapsed time, namely it had very high stability.

EXAMPLE 53

Foundation constituted of the following ingredients was prepared in accordance with the process described below:

| | Ingredients | Amount mixed (wt %) |
|---|---|---|
| 1. | Decamethylcyclopentasiloxane | 27.0 |
| 2. | Methylphenylpolysiloxane | 3.0 |
| 3. | Glyceryl triisooctanoate | 10.0 |
| 4. | Silicone compound of Example 9 | 1.0 |
| 5. | Polyglyceryl monoisostearate | 3.0 |
| 6. | Mixed powder treated so as to have hydrophobility (*1) | 18.0 |
| 7. | Iron oxide red | 1.2 |
| 8. | Iron oxide yellow | 2.6 |
| 9. | Iron oxide black | 0.2 |
| 10. | 1,3-Butylene glycol | 7.0 |

-continued

|  | Ingredients | Amount mixed (wt %) |
|---|---|---|
| 11. | Sodium chloride | 0.5 |
| 12. | Antiseptic | proper |
| 13. | Perfume | proper |
| 14. | Purified water | the rest |

(*1) powder prepared by mixing (a) 8.0 wt % of fine-grain titanium dioxide, (b) 4.0 wt % of fine-grain zinc oxide, (c) 3.0 wt % of talc and (d) 3.0 wt % of mica, adding thereto 1 wt % of methylhydrogenpolysiloxane, and subjecting the admixture to heat treatment.

[Preparation Process]

A: The ingredients 1 to 5 were mixed and dissolved under heating, and therein the ingredient 6 to 9 were dispersed homogeneously.

B: The ingredients 10 to 12 and 14 were mixed together, and then added to the dispersion obtained in the step A, followed by emulsifying treatment.

C: After the emulsion obtained in the step B was cooled, the ingredient 13 was added thereto.

The thus prepared foundation had no tacky feel, not only spread smoothly but also provided clingy feeling and fitted in with the skin, and further had lustrous finish and durable makeup effects. In addition, it was confirmed that the present foundation caused no change in quality by temperature changes and lapsed time, namely it had very high stability.

EXAMPLE 54

A makeup remover constituted of the following ingredients was prepared in accordance with the process described below:

|  | Ingredients | Amount mixed (wt %) |
|---|---|---|
| 1. | Silicone compound of Example 2 | 20.0 |
| 2. | Sorbitan polyoxyethylene(20) monostearate | 10.0 |
| 3. | Sorbitol | 10.0 |
| 4. | Carrageenan | 0.5 |
| 5. | Antiseptic | proper |
| 6. | Perfume | proper |
| 7. | Purified water | the rest |

[Preparation Process]

A: The ingredients 1 to 5 and 7 were mixed together to prepare a homogeneous solution.

B: The ingredient 6 was added to the solution obtained in the step A.

When durable foundation was rubbed off with the thus prepared makeup remover, this makeup remover was absorbed well by the foundation and sebum stains to result in effective removal thereof. Further, the remover spread well and had no sticky feel, but it left a refreshed feel to the users after it was wiped off. In other words, this remover had excellent usability and provided a pleasant feel to the users. In addition, it was confirmed that the remover caused no change in quality by temperature changes and elapsed time, namely it had high stability.

EXAMPLE 55

A hair makeup remover constituted of the following ingredients was prepared in accordance with the process described below:

|  | Ingredients | Amount mixed (wt %) |
|---|---|---|
| 1. | Silicone compound of Example 6 | 10.0 |
| 2. | Diethylene glycol monoethyl ether | 5.0 |
| 3. | Glycerin | 30.0 |
| 4. | Carrageenan | 0.5 |
| 5. | Antiseptic | proper |
| 6. | Perfume | proper |
| 7. | Purified water | the rest |

[Preparation Process]

A: The ingredients 1 to 5 and 7 were mixed together to prepare a homogeneous solution.

B: The ingredient 6 was added to the solution obtained in the step A.

The hair was washed with the thus prepared hair-makeup remover. As a result, it was found that the hair makeup and the sebum stains was absorbed well by this remover, and so they came out easily. Further, the remover spread well when applied to the hair, and had no sticky feel but left a refreshed feel to the users after it was washed out. In other words, this remover had excellent usability and provided a pleasant feel to the users. In addition, it was confirmed that the remover caused no change in quality by temperature changes and elapsed time, namely it had high stability.

EXAMPLE 56

Sun cut cream constituted of the following ingredients was prepared in accordance with the process described below:

|  | Ingredients | Amount mixed (wt %) |
|---|---|---|
| 1. | Decamethylcyclopentasiloxane | 17.5 |
| 2. | KP545 (*1) | 12.0 |
| 3. | Glyceryl triisooctanoate | 5.0 |
| 4. | Octyl paramethoxycinnamate | 6.0 |
| 5. | KSG21 (*2) | 5.0 |
| 6. | Silicone compound of Example 1 | 1.0 |
| 7. | Zinc oxide treated so as to have affinity for oil | 20.0 |
| 8. | Sodium chloride | 0.5 |
| 9. | 1,3-Butylene glycol | 2.0 |
| 10. | Antiseptic | proper |
| 11. | Perfume | proper |
| 12. | Purified water | the rest |

(*1) Acrylsilicone produced by SHIN-ETSU CHEMICAL Co., Ltd.
(*2) Silicone gel produced by SHIN-ETSU CHEMICAL Co., Ltd.

[Preparation Process]

A: The ingredient 2 was added to a part of the ingredient 1, and these ingredients were homogenized. Therein, the ingredient 7 was admixed, and dispersed by means of a beads mill.

B: The rest of the ingredient 1 and the ingredients 3 to 6 were mixed together to make a homogeneous mixture.

C: The ingredients 8 to 10 and 12 were mixed and dissolved.

D: The mixture obtained in the step B was added to the solution obtained in the step C, followed by emulsifying treatment. To the emulsion obtained, the dispersion obtained in the step A and the ingredient 11 were further added.

The thus prepared sun cut cream had no tacky feel, not only spread smoothly but also provided clingy feeling and fitted in with the skin, and further ensured lustrous finish and durable makeup effects. In addition, it was confirmed that the present cream caused no change in quality by of temperature changes and lapsed time, namely it had very high stability.

EXAMPLE 57

Oil-in-water hand cream constituted of the following ingredients was prepared in accordance with the process described below:

| | Ingredients | Amount mixed (wt %) |
|---|---|---|
| 1. | KP545 (*1) | 10.0 |
| 2. | KSG16 (*2) | 2.0 |
| 3. | Isoparaffin | 5.0 |
| 4. | Vaseline | 5.0 |
| 5. | Glyceryl triisooctanoate | 3.0 |
| 6. | Silicone compound of Example 1 | 0.5 |
| 7. | Polyoxyethylenesorbitan monooleate | 1.0 |
| 8. | Seppigel 305 (*3) | 2.0 |
| 9. | 1,3-Butylene glycol | 5.0 |
| 10. | Antiseptic | proper |
| 11. | Perfume | proper |
| 12. | Purified water | the rest |

(*1) Acrylsilicone produced by SHIN-ETSU CHEMICAL Co., Ltd.
(*2) Silicone gel produced by SHIN-ETSU CHEMICAL Co., Ltd.
(*3) A product of SEPPIC CO., LTD.

[Preparation Process]
A: The ingredients 1 to 7 were mixed homogeneously.
B: The ingredients 8 to 11 and 13 were mixed homogeneously.
C: The mixture obtained in the step B was added to the mixture obtained in the step A, thereby making an emulsion. To the emulsion obtained, the ingredient 12 was further added.

The thus prepared oil-in-water hand cream had no tacky feel, not only spread smoothly but also provided a clingy feeling and fitted in with the skin, and further ensured lustrous finish and durable effects. In addition, it was confirmed that the present cream was very stable to temperature changes and lapsed time.

EXAMPLE 58

Oil-in-water hand cream constituted of the following ingredients was prepared in accordance with the process described below:

| | Ingredients | Amount mixed (wt %) |
|---|---|---|
| 1. | KP545 (*1) | 10.0 |
| 2. | KP561 (*2) | 8.0 |
| 3. | Cetanol | 1.0 |
| 4. | Glyceryl triisostearate | 5.0 |
| 5. | Stearic acid | 3.0 |
| 6. | Glyceryl monostearate | 1.5 |
| 7. | Silicone compound of Example 1 | 0.7 |
| 8. | Sorbitan sesqui-oleate | 0.5 |
| 9. | Polyoxyethylenesorbitan monooleate | 1.0 |
| 10. | Sodium hydroxide (1% aq. soln.) | 10.0 |
| 11. | 1,3-Butylene glycol | 5.0 |
| 12. | Antiseptic | proper |

| | Ingredients | Amount mixed (wt %) |
|---|---|---|
| 13. | Perfume | proper |
| 14. | Purified water | the rest |

(*1) Acrylsilicone produced by SHIN-ETSU CHEMICAL Co., Ltd.
(*2) Stearyl-modified acrylsilicone produced by SHIN-ETSU CHEMICAL Co., Ltd.

[Preparation Process]
A: The ingredients 1 to 9 were mixed and made into a solution under heating.
B: The ingredients 10 to 12 and 14 were mixed and heated.
C: The mixture obtained in the step B was added to the solution obtained in the step A, thereby making an emulsion. After cooling the emulsion, the ingredient 13 was further added thereto.

The thus prepared oil-in-water hand cream had no tacky feel, not only spread smoothly but also provided a clingy feeling and fitted in with the skin, and further ensured lustrous finish and durable effects. In addition, it was confirmed that the present cream was very stable to temperature changes and lapsed time.

ADVANTAGES OF THE INVENTION

The present cosmetic materials in which are mixed silicone compounds represented by formula (1) according to the invention have no oily feel although they spread easily and smoothly, give moist, fresh and dry feelings to the users, and besides, have durable effects and are highly stable to temperature changes and long-term storage. In addition, the skin-cleansing compositions in which are mixed the present silicone compounds have not only the aforementioned excellent feels, usability and storage stability but also well absorb makeup cosmetics and sebum stains, and so they can have very good cleaning effects.

What is claimed is:

1. A silicone compound that is non-cross linked, represented by formula (1):

$$R^1_a R^2_b R^3_c SiO_{(4-a-b-c)/2} \quad (1)$$

wherein $R^1$ groups are independently each an organic 1–30C alkyl, aryl, aralkyl, or fluorinated alkyl groups or an organic group of formula (2), $$-C_m H_{2m}-O-(C_2H_4O)_d(C_3H_6O)_e R^4 \quad (2);$$

$R^2$ groups are independently polyoxyalkylene moiety-containing organic groups of formula (3), $$-C_m H_{2m}-O-(C_2H_4O)_f(C_3H_6O)_g R^5 \quad (3);$$

$R^3$ groups are independently organosiloxane compound residues of formula (4),

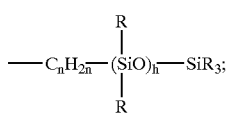

(4)

R is a 1–30C alkyl group, an aryl group, or a fluorinated alkyl group;

$R^4$ is a 4–30C hydrocarbon or an acyl of formula $R^6$—CO—;

$R^5$ is a hydrogen atom, a 1–30C hydrocarbon or an acyl of formula $R^6$—CO—;

$R^6$ is a 1–30C hydrocarbon; a, b and c are values in the ranges $1.0 \leq a \leq 2.5$, $0.001 \leq b \leq 1.5$ and $0.001 \leq c \leq 1.5$; d and e are integers of 0 to 50; f is an integer of 2 to 200; g is an integer of 0 to 200, wherein the sum of f and g is an integer of 3 to 200; m is an integer of 0 to 15; h is an integer of 0 to 500; and n is an integer of 1 to 5.

2. A silicone compound that is non-cross linked, represented by formula (1):

wherein $R^1$ groups are independently each an organic 1–30C alkyl, aryl, aralkyl, or fluorinated alkyl groups or an organic group of formula (2),

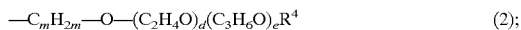

$R^2$ groups are independently polyoxyalkylene moiety-containing organic groups of formula (3),

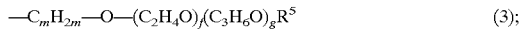

$R^3$ groups are independently organosiloxane compound residues of formula (4),

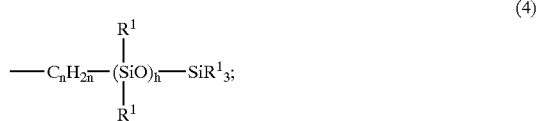

$R^4$ is a 4–30C hydrocarbon or an acyl of formula $R^6$—CO—;

$R^5$ is a hydrogen atom, a 1–30C hydrocarbon or an acyl of formula $R^6$—CO—;

$R^6$ is a 1–30C hydrocarbon; a, b and c are values in the ranges $1.0 \leq a \leq 2.5$, $0.001 \leq b \leq 1.5$ and $0.001 \leq c \leq 1.5$; d and e are integers of 0 to 50; f is an integer of 2 to 200; g is an integer of 0 to 200, wherein the sum of f and g is an integer of 3 to 200; m is an integer of 0 to 15; h is an integer of 0 to 500; and n is an integer of 1 to 5.

3. A silicone compound according to claim 2, wherein at least 50% of R1 groups are methyl groups.

4. A silicone compound according to claim 2, having a weight average molecular weight in the range of 500 to 200,000.

5. A cosmetic material comprising a silicone compound described in claim 2.

6. A cosmetic material according to claim 5, wherein the silicone compound represented by formula (1) of claim 2 comprises a proportion of 0.1 to 40% by weight of the total ingredients in the cosmetic material.

7. A skin-cleansing composition comprising a silicone compound of claim 2.

8. A silicone compound of claim 2, wherein d and e are zero and m is 3, 5 or 11.

9. A silicone compound of claim 2, wherein m is an integer of 3 to 11.

10. A silicone compound according to claim 2, wherein at least 70% of $R^1$ groups are methyl groups.

11. A silicone compound of claim 2, wherein $f/g \geq 1$.

12. A silicone compound of claim 2, wherein h is an integer of 3 to 100.

13. A silicone compound of claim 2, wherein a has a value of 1.2 to 2.3.

14. A silicone compound of claim 2, wherein b has a value of 0.05 to 1.0.

15. A silicone compound of claim 2, wherein c has a value of 0.5 to 1.0.

16. A silicone compound according to claim 7, having a weight average molecular weight in the range of 1000 to 100,000.

17. A skin-cleansing composition according to claim 7, having a weight average molecular weight at most of 4,000.

18. A skin-cleansing composition according to claim 17, having a weight average molecular weight at most of 2,000.

19. A cosmetic material according to claim 5, wherein the cosmetic material is in a form which is applicable to skin and/or hair.

20. A silicone compound of claim 2, wherein $R^1$ is methyl, ethyl, propyl, butyl, pentyl, hexyl, heptyl octyl, nonyl, decyl, cyclopentyl and cyclohexyl groups; those of an aryl group are phenyl or tolyl groups; those of an aralkyl group are benzyl or phenethyl groups; and those of a fluorinated alkyl group are trifluoropropyl, or heptadecafluorodecyl groups, and the organic group —$C_mH_{2m}$—O—$(C_2H_4O)_d(C_3H_6O)_eR^4$ is an alkoxy group, an acyloxy group, an alkenyl ether residue and an alkenyl ester residue.

21. A method of cleaning sebum and makeup stains comprising applying to the skin the skin-cleansing composition of claim 7.

* * * * *